(12) United States Patent
Byers

(10) Patent No.: US 11,484,618 B2
(45) Date of Patent: Nov. 1, 2022

(54) VAPOR GENERATION AND DISTRIBUTION DEVICES, SYSTEMS, AND METHODS

(71) Applicant: KGM Enterprises, Inc., Bloomington, IN (US)

(72) Inventor: Marc L. Byers, Bloomington, IN (US)

(73) Assignee: KGM Enterprises, Inc., Bloomington, IN (US)

( * ) Notice: Subject to any disclaimer, the term of this patent is extended or adjusted under 35 U.S.C. 154(b) by 231 days.

(21) Appl. No.: 16/897,223

(22) Filed: Jun. 9, 2020

(65) Prior Publication Data

US 2020/0306403 A1     Oct. 1, 2020

Related U.S. Application Data

(63) Continuation-in-part of application No. 15/755,970, filed as application No. PCT/US2016/049217 on Aug. 29, 2016, now Pat. No. 10,675,372.

(60) Provisional application No. 62/377,735, filed on Aug. 22, 2016, provisional application No. 62/334,252, filed on May 10, 2016, provisional application No. 62/210,466, filed on Aug. 27, 2015.

(51) Int. Cl.
    *A61L 9/05*     (2006.01)
    *A61L 9/12*     (2006.01)

(52) U.S. Cl.
    CPC ............ *A61L 9/05* (2013.01); *A61L 9/12* (2013.01); *A61L 2209/134* (2013.01)

(58) Field of Classification Search
    CPC ............ A61L 9/122; A61L 2209/111; A61L 2209/11; A61L 9/032; B01D 1/0082; B01D 1/0011
    See application file for complete search history.

(56) References Cited

U.S. PATENT DOCUMENTS

| | | | |
|---|---|---|---|
| 6,167,318 A | 12/2000 | Kizer | |
| 6,379,242 B1 | 4/2002 | Wiseman, Sr. et al. | |
| 6,770,247 B1 | 8/2004 | Romack et al. | |
| 7,638,114 B1 | 12/2009 | Schur | |
| 2002/0018181 A1 | 2/2002 | Manne | |
| 2006/0269455 A1 | 11/2006 | Planker | |
| 2010/0301123 A1 | 12/2010 | Dorendorf | |
| 2012/0114587 A1* | 5/2012 | Slutz | A61L 9/145 424/76.5 |

(Continued)

OTHER PUBLICATIONS

International Searching Authority, International Search Report, PCT/US2016/049217, dated Dec. 1, 2016.

(Continued)

*Primary Examiner* — Sean E Conley
*Assistant Examiner* — Brendan A Hensel
(74) *Attorney, Agent, or Firm* — Reichel Stohry Dean LLP; Mark C. Reichel; Natalie J. Dean

(57) ABSTRACT

Vapor generation and distribution devices, systems, and methods. An exemplary system of the present disclosure comprises a vapor generation system configured to volatilize or vaporize liquid chemical within a tank as volatilized or vaporized chemical, and a vapor distribution system configured to receive the volatilized or vaporized chemical from the vapor generation system and distribute the volatilized or vaporized chemical through a distribution conduit coupled to the second air flow generator.

20 Claims, 24 Drawing Sheets

(56) References Cited

U.S. PATENT DOCUMENTS

2013/0174842 A1  7/2013  Young et al.

OTHER PUBLICATIONS

International Searching Authority, Written Opinion of the International Searching Authority, PCT/US2016/049217, dated Dec. 1, 2016.

* cited by examiner

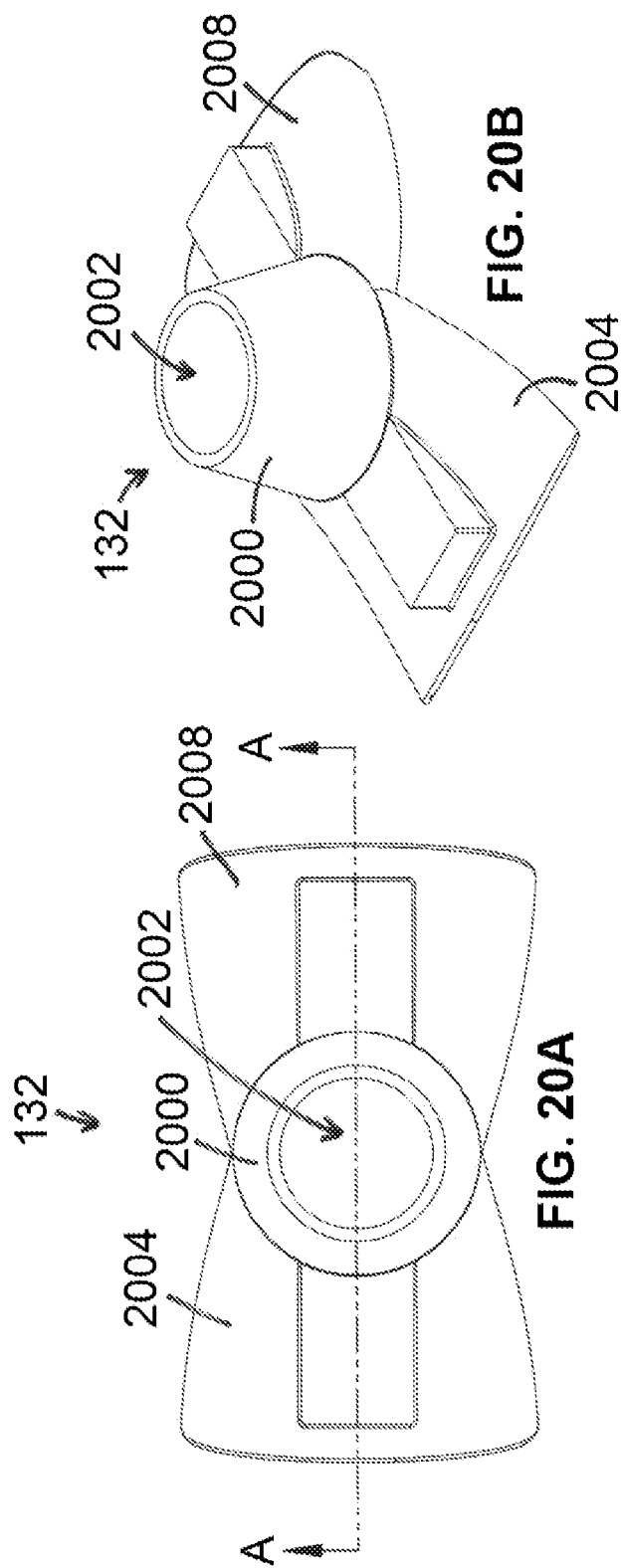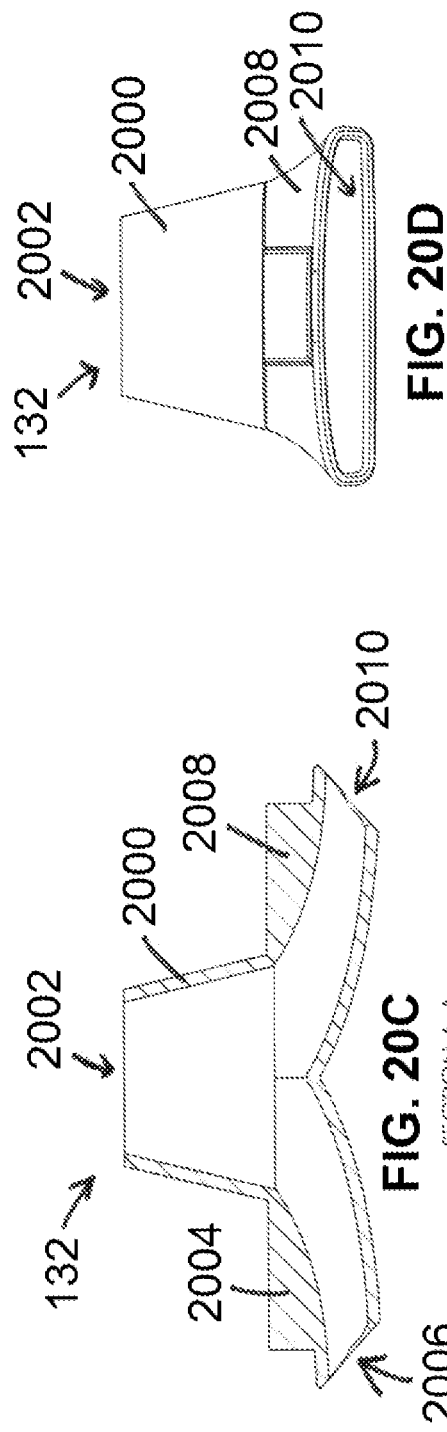

VAPOR GENERATION AND DISTRIBUTION DEVICES, SYSTEMS, AND METHODS

PRIORITY

The present application is related to, claims the priority benefit of, and is a U.S. continuation-in-part patent application of, U.S. patent application Ser. No. 15/755,970, filed Feb. 27, 2018 and issued as U.S. Pat. No. 10,675,372 on Jun. 9, 2020, which is related to, claims the priority benefit of, and is a U.S. 35 U.S.C. 371 national phase application of, International Patent Application Serial No. PCT/US2016/049217, filed Aug. 29, 2016, which is related to, and claims the priority benefit of, a) U.S. Provisional Patent Application Ser. No. 62/210,466, filed Aug. 27, 2015, b) U.S. Provisional Patent Application Ser. No. 62/334,252, filed May 10, 2016, and c) U.S. Provisional Patent Application Ser. No. 62/377,735, filed Aug. 22, 2016. The contents of each of the foregoing applications and patent are incorporated herein by reference in their entirety.

BACKGROUND

Landfills, farms, and other industrial/commercial locations that generate noxious or otherwise offensive odors not only make the immediate locations less than desirable due to said odors, but also cause surrounding areas, especially when wind is present, to also be impacted by said odors.

One way to address said odors is to introduce a chemical having its own odor, with the goal of masking the noxious or offensive odor with a more pleasant odor. Another way is to introduce some sort of chemical that reacts with the noxious or offensive odor to neutralize or otherwise reduce the severity of said noxious or otherwise offensive odor.

Systems currently on the market used to distribute said chemicals have various pitfalls, as will be provided in further detail herein. For example, some systems are not properly sized or powered to create a desired laminar flow. Other systems simply cannot generate a necessary amount of volatilized/vaporized chemical from a quantity of liquid chemical to effectively address the noxious or offensive odors.

In view of the foregoing, devices, systems, and methods useful to generate and distribute chemical vapor in an efficient and effective manner to address and solve the problems of noxious or otherwise offensive odors would be well received in the marketplace.

BRIEF SUMMARY

The present disclosure includes disclosure of a system, comprising an air flow generator configured to generate a flow of air; a first outlet conduit configured to deliver the flow of air from the air flow generator into a tank having a quantity of liquid chemical therein; and a flotation element positioned within the tank and defining an aperture therein, the flotation element configured to float upon the quantity of liquid chemical within the tank so that the flow of air from the first outlet conduit passes through the aperture of the flotation element and is directed onto a surface of the liquid chemical; wherein the flow of air causes at least a portion of the quantity of liquid chemical to volatilize or vaporize as volatilized or vaporized chemical and exit the tank from a tank aperture.

The present disclosure includes disclosure of a system, wherein the flotation element is configured so that when the flotation element is floating upon the quantity of liquid chemical, a distance between the aperture of the flotation element and the surface of the quantity of liquid chemical remains constant or generally constant. The present disclosure includes disclosure of a system, wherein the aperture of the flotation element is located within flotation element so that when the flotation element is floating upon the quantity of liquid chemical, a distance exists between the aperture of the flotation element and a surface of the quantity of liquid chemical. The present disclosure includes disclosure of a system, further comprising an air flow reducer positioned between the air flow generator and the first outlet conduit, the air flow reducer configured to concentrate the flow of air from the air flow generator prior to the flow of air entering the first outlet conduit.

The present disclosure includes disclosure of a system, further comprising an air flow velocity controller positioned between the air flow generator and the first outlet conduit, the air flow velocity controller configured to control a rate of the flow of air from the air flow generator prior to the flow of air entering the first outlet conduit. The present disclosure includes disclosure of a system, wherein the first outlet conduit is flexible. The present disclosure includes disclosure of a system, further comprising a second outlet conduit coupled to the first outlet conduit and the flotation element, the second outlet conduit configured to fit within and slidingly engage a conduit aperture defined within the tank or defined within a tank lid. The present disclosure includes disclosure of a system, wherein the second outlet conduit is rigid.

The present disclosure includes disclosure of a system, further comprising an air flow reducer positioned between the air flow generator and the first outlet conduit, the air flow reducer configured to concentrate the flow of air from the air flow generator prior to the flow of air entering the first outlet conduit; an air flow velocity controller positioned between the air flow reducer and the first outlet conduit, the air flow velocity controller configured to control a rate of the flow of air from the air flow generator prior to the flow of air entering the first outlet conduit; and a second outlet conduit coupled to the first outlet conduit and the flotation element, the second outlet conduit configured to fit within and slidingly engage a conduit aperture defined within the tank or defined within a tank lid; wherein the flow of air from the air flow generator, during operation of the air flow generator, passes through the air flow reducer, through the air flow velocity controller, through the first outlet conduit, through the second outlet conduit, and through the aperture of the flotation element onto the surface of the liquid chemical.

The present disclosure includes disclosure of a system, further comprising a second air flow generator having an inlet and positioned relative to the tank; and an inlet conduit having a proximal end and a distal end defining a distal opening, the proximal end of the inlet conduit coupled to the tank at the tank aperture and the distal opening positioned relative to the inlet of the second air flow generator; the second air flow generator configured receive the volatilized or vaporized chemical from the tank through the inlet conduit and to distribute the volatilized or vaporized chemical through a distribution conduit coupled to the second air flow generator.

The present disclosure includes disclosure of a system, wherein the second air flow generator comprises a motor positioned within a housing, and wherein the inlet of the second air flow generator is defined within the housing. The present disclosure includes disclosure of a system, wherein the distal opening of the inlet conduit does not completely cover the inlet of the second air flow generator. The present disclosure includes disclosure of a system, wherein the distribution conduit has a plurality of apertures defined therein. The present disclosure includes disclosure of a system, wherein the distribution conduit is coupled to a second distribution conduit, and wherein the second distribution conduit has a plurality of apertures defined therein. The present disclosure includes disclosure of a system, wherein the distribution conduit is coupled to a second distribution conduit, and wherein the second distribution conduit is coupled to a third distribution conduit and a fourth distribution conduit, and wherein the third distribution conduit and the fourth distribution conduit each have a plurality of apertures defined therein.

The present disclosure includes disclosure of a system, further comprising at least one stand, the at least one stand positioned between the distribution conduit and a ground surface. The present disclosure includes disclosure of a system, wherein the air flow velocity controller comprises a ball valve. The present disclosure includes disclosure of a system, wherein the air flow velocity controller comprises a gate valve.

The present disclosure includes disclosure of a system, further comprising a gauge configured to measure static pressure, the gauge connected to the system proximal to and distal to the air flow velocity controller. The present disclosure includes disclosure of a system, further comprising a gauge configured to measure static pressure, the gauge connected to the system proximal to and distal to the air flow reducer.

The present disclosure includes disclosure of a system, wherein the flotation element has a second aperture defined therein, and wherein the flow of air from the first outlet conduit passes through the aperture and the second aperture of the flotation element onto the surface of the liquid chemical.

The present disclosure includes disclosure of a system, further comprising a feeder tank having a second quantity of liquid chemical therein; and a pump having a feeder tube, the pump configured to pump at least some of the second quantity of liquid chemical from the feeder tank through the feeder tube, through a pump distribution tube coupled to the pump or the feeder tube, and into the tank.

The present disclosure includes disclosure of a system, further comprising a heater positioned relative to the tank and configured to raise a temperature of the quantity of liquid chemical within the tank. The present disclosure includes disclosure of a system, further comprising a heater positioned relative to the feeder tank and configured to raise a temperature of the second quantity of liquid chemical within the feeder tank.

The present disclosure includes disclosure of a system, wherein the gauge comprises a wireless transmitter configured to transmit pressure data from the gauge to a remote location. The present disclosure includes disclosure of a system, further comprising a level sensor configured to obtain data relating to a level of the quantity of the first chemical within the tank, wherein said data is used to control operation of the pump.

The present disclosure includes disclosure of a system, further comprising an air flow reducer positioned between the air flow generator and the first outlet conduit, the air flow reducer configured to concentrate the flow of air from the air flow generator prior to the flow of air entering the first outlet conduit; an air flow velocity controller positioned between the air flow reducer and the first outlet conduit, the air flow velocity controller configured to control a rate of the flow of air from the air flow generator prior to the flow of air entering the first outlet conduit; and a second outlet conduit coupled to the first outlet conduit and the flotation element, the second outlet conduit configured to fit within and slidingly engage a conduit aperture defined within the tank or defined within a tank lid; wherein the flow of air from the air flow generator, during operation of the air flow generator, passes through the air flow reducer, through the air flow velocity controller, through the first outlet conduit, through the second outlet conduit, and through the aperture of the flotation element onto the surface of the liquid chemical; and wherein the distribution conduit is coupled to a second distribution conduit, and wherein the second distribution conduit has a plurality of apertures defined therein. The present disclosure includes disclosure of a system, wherein when the distribution conduit or a second distribution conduit coupled thereto is positioned relative to a source of an odor, the volatilized or vaporized chemical distributed by the second air flow generator can exit a plurality of apertures defined within the distribution conduit and/or the second distribution conduit to alleviate the odor.

The present disclosure includes disclosure of an overall system, comprising an exemplary vapor generation system of the present disclosure and an exemplary vapor distribution system of the present disclosure.

The present disclosure includes disclosure of a method to generate vapor, comprising the step of operating a vapor generation system to generate volatilized or vaporized chemical. The present disclosure includes disclosure of a method to distribute vapor, comprising the step of operating a vapor distribution system to distribute volatilized or vaporized chemical.

The present disclosure includes disclosure of a system, comprising an air flow generator configured to generate a flow of air; a first outlet conduit configured to deliver the flow of air from the air flow generator into a tank having a quantity of liquid chemical therein; and a flotation element positioned within the tank and defining an aperture therein, the flotation element comprising at least two buoyant elements configured to float upon the quantity of liquid chemical within the tank; a support panel having an aperture defined therethrough, the support pane configured for coupling to the at least two buoyant elements and further configured to receive at least part of a diffusion portion therethrough; and the diffusion portion comprising an inlet aperture, a first outlet portion, and a second outlet portion opposite the first outlet portion; the flotation element configured so that the flow of air from the first outlet conduit passes through the inlet aperture of the diffusion portion and out of the first outlet portion and the second outlet portion to direct the flow of air horizontally across the surface of the liquid chemical; wherein the flow of air causes at least a portion of the quantity of liquid chemical to volatilize or vaporize as volatilized or vaporized chemical and exit the tank from a tank aperture.

The present disclosure includes disclosure of a system, wherein the flotation element is configured so that when portions of the flotation element are floating upon the quantity of liquid chemical, a distance between the inlet aperture of the diffusion portion and the surface of the quantity of liquid chemical remains constant or generally constant.

The present disclosure includes disclosure of a system, wherein the inlet aperture of the diffusion portion of the flotation element is located so that when portions of the flotation element are floating upon the quantity of liquid chemical, a distance exists between the inlet aperture and a surface of the quantity of liquid chemical.

The present disclosure includes disclosure of a system, further comprising an air flow velocity controller positioned between the air flow generator and the first outlet conduit, the air flow velocity controller configured to control a rate of the flow of air from the air flow generator prior to the flow of air entering the first outlet conduit.

The present disclosure includes disclosure of a system, further comprising a second outlet conduit coupled to the first outlet conduit and the flotation element, the second outlet conduit configured to fit within and slidingly engage a conduit aperture defined within the tank or defined within a tank lid.

The present disclosure includes disclosure of a system, further comprising an air flow reducer positioned between the air flow generator and the first outlet conduit, the air flow reducer configured to concentrate the flow of air from the air flow generator prior to the flow of air entering the first outlet conduit; an air flow velocity controller positioned between the air flow reducer and the first outlet conduit, the air flow velocity controller configured to control a rate of the flow of air from the air flow generator prior to the flow of air entering the first outlet conduit; and a second outlet conduit coupled to the first outlet conduit and the flotation element, the second outlet conduit configured to fit within and slidingly engage a conduit aperture defined within the tank or defined within a tank lid; wherein the flow of air from the air flow generator, during operation of the air flow generator, passes through the air flow reducer, through the air flow velocity controller, through the first outlet conduit, through the second outlet conduit, and through the inlet aperture of the diffusion portion of the flotation element and onto the surface of the liquid chemical.

The present disclosure includes disclosure of a system, further comprising a second air flow generator having an inlet and positioned relative to the tank; an inlet conduit having a proximal end and a distal end defining a distal opening, the proximal end of the inlet conduit coupled to the tank at a tank aperture and the distal opening positioned relative to the inlet of the second air flow generator; an intake extending from the inlet of the second air flow generator; and a nozzle positioned at the distal opening of the distal end of the inlet conduit; the second air flow generator configured to receive the volatilized or vaporized chemical from the tank through the inlet conduit and through the nozzle to an inside of the intake and ultimately into the inlet of the second air flow generator and to distribute the volatilized or vaporized chemical through a distribution conduit coupled to the second air flow generator.

The present disclosure includes disclosure of a system, wherein the second air flow generator comprises a motor positioned within a housing, and wherein the inlet of the second air flow generator is defined within the housing.

The present disclosure includes disclosure of a system, wherein the distribution conduit has a plurality of apertures defined therein.

The present disclosure includes disclosure of a system, wherein the distribution conduit is coupled to a second distribution conduit, and wherein the second distribution conduit has a plurality of apertures defined therein.

The present disclosure includes disclosure of a system, further comprising a gauge configured to measure static pressure, the gauge connected to the system proximal to and distal to the air flow velocity controller.

The present disclosure includes disclosure of a system, further comprising a feeder tank having a second quantity of liquid chemical therein; and a pump having a feeder tube, the pump configured to pump at least some of the second quantity of liquid chemical from the feeder tank through the feeder tube, through a pump distribution tube coupled to the pump or the feeder tube, and into the tank.

The present disclosure includes disclosure of a system, further comprising a heater positioned relative to the tank and configured to raise a temperature of the quantity of liquid chemical within the tank.

The present disclosure includes disclosure of a system, further comprising a heater positioned relative to the feeder tank and configured to raise a temperature of the second quantity of liquid chemical within the feeder tank.

The present disclosure includes disclosure of a system, wherein the gauge comprises a wireless transmitter configured to transmit pressure data from the gauge to a remote location.

The present disclosure includes disclosure of a system, further comprising a level sensor configured to obtain data relating to a level of the quantity of the first chemical within the tank, wherein said data is used to control operation of the pump.

The present disclosure includes disclosure of a system, further comprising an air flow reducer positioned between the air flow generator and the first outlet conduit, the air flow reducer configured to concentrate the flow of air from the air flow generator prior to the flow of air entering the first outlet conduit; an air flow velocity controller positioned between the air flow reducer and the first outlet conduit, the air flow velocity controller configured to control a rate of the flow of air from the air flow generator prior to the flow of air entering the first outlet conduit; and a second outlet conduit coupled to the first outlet conduit and the flotation element, the second outlet conduit configured to fit within and slidingly engage a conduit aperture defined within the tank or defined within a tank lid; wherein the flow of air from the air flow generator, during operation of the air flow generator, passes through the air flow reducer, through the air flow velocity controller, through the first outlet conduit, through the second outlet conduit, and through the aperture of the flotation element onto the surface of the liquid chemical; and wherein the distribution conduit is coupled to a second distribution conduit, and wherein the second distribution conduit has a plurality of apertures defined therein.

The present disclosure includes disclosure of a system, wherein when the distribution conduit or a second distribution conduit coupled thereto is positioned relative to a source of an odor, the volatilized or vaporized chemical distributed by the second air flow generator can exit a plurality of apertures defined within the distribution conduit and/or the second distribution conduit to alleviate the odor.

The present disclosure includes disclosure of a system, comprising a vapor generation system, comprising an air flow generator configured to generate a flow of air; a first outlet conduit configured to deliver the flow of air from the air flow generator into a tank having a quantity of liquid chemical therein; and a flotation element positioned within the tank and defining an aperture therein, the flotation element comprising at least two buoyant elements configured to float upon the quantity of liquid chemical within the tank; a support panel having an aperture defined therethrough, the support pane configured for coupling to the at least two buoyant elements and further configured to receive at least part of a diffusion portion therethrough; and the diffusion portion comprising an inlet aperture, a first outlet portion, and a second outlet portion opposite the first outlet portion; the flotation element configured so that the flow of air from the first outlet conduit passes through the inlet aperture of the diffusion portion and out of the first outlet portion and the second outlet portion to direct the flow of air horizontally across the surface of the liquid chemical; wherein the flow of air causes at least a portion of the quantity of liquid chemical to volatilize or vaporize as volatilized or vaporized chemical and exit the tank from a tank aperture; and a vapor distribution system, comprising a second air flow generator having an inlet and positioned relative to the tank; an inlet conduit having a proximal end and a distal end defining a distal opening, the proximal end of the inlet conduit coupled to the tank at a tank aperture and the distal opening positioned relative to the inlet of the second air flow generator; an intake extending from the inlet of the second air flow generator; and a nozzle positioned at the distal opening of the distal end of the inlet conduit; the second air flow generator configured to receive the volatilized or vaporized chemical from the tank through the inlet conduit and through the nozzle to an inside of the intake and ultimately into the inlet of the second air flow generator and to distribute the volatilized or vaporized chemical through a distribution conduit coupled to the second air flow generator.

The present disclosure includes disclosure of a method to generate vapor, comprising the step of operating a vapor generation system to generate volatilized or vaporized chemical, the vapor generation system comprising an air flow generator configured to generate a flow of air; a first outlet conduit configured to deliver the flow of air from the air flow generator into a tank having a quantity of liquid chemical therein; and a flotation element positioned within the tank and defining an aperture therein, the flotation element comprising at least two buoyant elements configured to float upon the quantity of liquid chemical within the tank; a support panel having an aperture defined therethrough, the support pane configured for coupling to the at least two buoyant elements and further configured to receive at least part of a diffusion portion therethrough; and the diffusion portion comprising an inlet aperture, a first outlet portion, and a second outlet portion opposite the first outlet portion; the flotation element configured so that the flow of air from the first outlet conduit passes through the inlet aperture of the diffusion portion and out of the first outlet portion and the second outlet portion to direct the flow of air horizontally across the surface of the liquid chemical; wherein the flow of air causes at least a portion of the quantity of liquid chemical to volatilize or vaporize as volatilized or vaporized chemical and exit the tank from a tank aperture.

BRIEF DESCRIPTION OF THE DRAWINGS

The disclosed embodiments and other features, advantages, and disclosures contained herein, and the matter of attaining them, will become apparent and the present disclosure will be better understood by reference to the following description of various exemplary embodiments of the present disclosure taken in conjunction with the accompanying drawings, wherein:

FIG. 20A shows a top down view of a flotation element, according to an exemplary embodiment of the present disclosure.

FIG. 20B shows a perspective view of the flotation element of FIG. 20A, according to an exemplary embodiment of the present disclosure.

FIG. 20C shows a cut-away side view of the flotation element of FIG. 20A, according to an exemplary embodiment of the present disclosure.

FIG. 20D shows an end view of the flotation element of FIG. 20A, according to an exemplary embodiment of the present disclos

Figure 1:
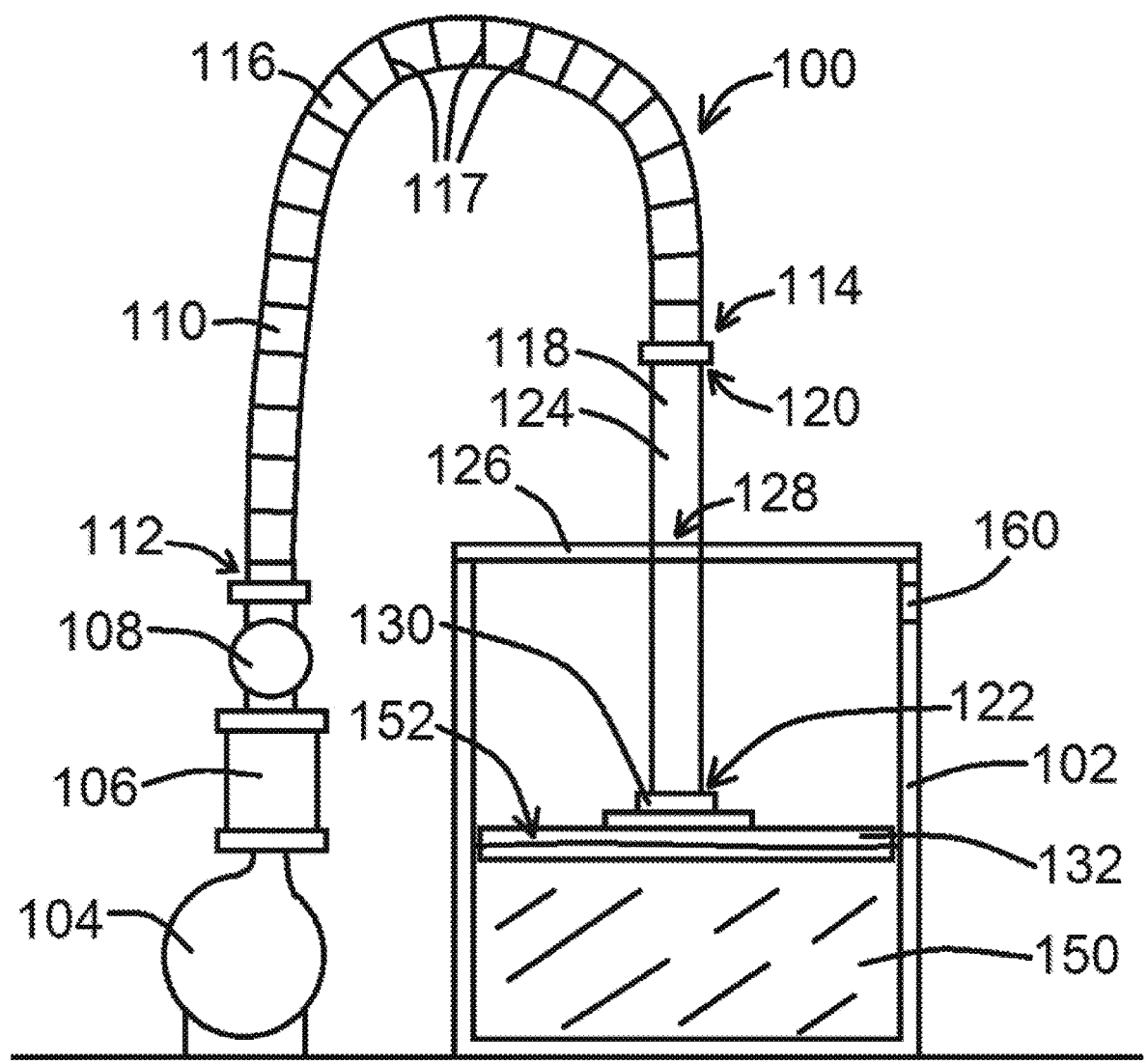
FIG. 1 shows components of a vapor generation system, according to an exemplary embodiment of the present disclosure.

An overview of the features, functions and/or configurations of the components depicted in the various figures will now be presented. It should be appreciated that not all of the features of the components of the figures are necessarily described. Some of these non-discussed features, such as various couplers, etc., as well as discussed features are inherent from the figures themselves. Other non-discussed features may be inherent in component geometry and/or configuration.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

The present disclosure includes disclosure of systems, devices, and methods for generating chemical vapor and distributing said vapor.

An exemplary system for generating chemical vapor of the present disclosure is shown in FIG. 1. As shown in FIG. 1, an exemplary vapor generation system 100 of the present disclosure comprises a tank 102 configured to retain a quantity of liquid chemical 150. Tank 102 can comprise any number of shapes, sizes, and materials, so long as a quantity of liquid chemical 150 can be retained therein. Vapor generation system 100, as referenced herein, further comprises an air flow generator 104, such as a fan or other device known or developed in the art configured to generate a positive flow of air in at least one direction.

In an exemplary embodiment of a vapor generation system 100 of the present disclosure, a mating flange 106, such as a device known or developed in the art configured to couple portions of ducting to one another, can be used to couple to air flow generator 104 to air flow velocity controller 108, such as shown in FIG. 1. Air flow velocity controller 108, such as a ball valve or other device known or developed in the art configured to allow for the control of the velocity of air flow, can be coupled to mating flange 106, such as shown in FIG. 1, to allow the user of the vapor generation system 100 to control the velocity of the air flow generated by air flow generator 104 through air flow velocity controller 108. Air flow velocity controller 108, in various embodiments, are configured to limit the flow of air to a desired level, operating as air flow reducers as needed. A flexible first outlet conduit 110, such as shown in FIG. 1, can be coupled to or otherwise positioned relative to air flow velocity controller 108 so that a positive air flow generated by air flow generator 104 can be directed through first outlet conduit 110 directly into tank 102, or, for example, into second outlet conduit 118 and ultimately into tank 102 as shown in FIG. 1.

Figure 4:
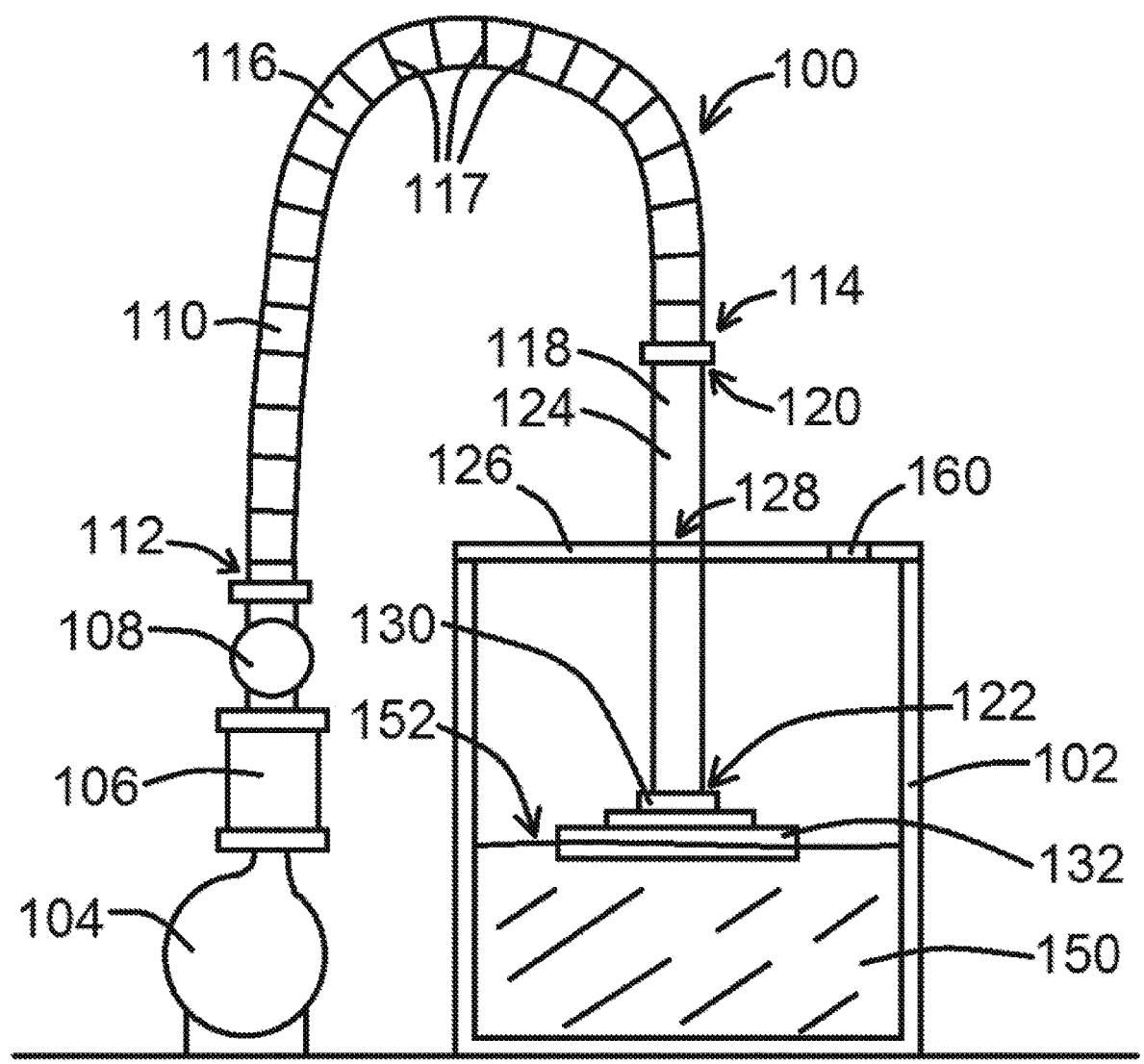
FIG. 4 shows components of a vapor generation system with a smaller flotation element than shown in FIG. 1, according to an exemplary embodiment of the present disclosure.

Exemplary first outlet conduits 110 of the present disclosure comprise a proximal end 112 and a distal end 114, and define a lumen 116 therethrough extending from proximal end 112 to distal end 114. Proximal end 112 of first outlet conduit 110 is configured to receive the positive air flow from air flow generator 104, either directly from air flow generator or after passing through mating flange 106 and air flow velocity controller 108, whereby the positive air flow is directed out of distal end 114 of first outlet conduit 110 to a second outlet conduit 118, such as shown in FIG. 1, or, in other embodiments, within tank 102. As shown in FIGS. 1 and 4, for example, a general angle of approach of distal end 114 of first outlet conduit 110 relative to second outlet conduit is zero in at least some preferred vapor generation system 100 embodiments. Corrugations 117 at a relative apex of the arc of first outlet conduits 110, such as shown in FIGS. 1 and 4, allow the free vertical travel/movement of that portion of assembly (distal end 114 of first outlet conduit 110 and second outlet conduit 118, for example).

As shown in FIG. 1, an exemplary rigid second outlet conduit 118 of the present disclosure may also be used with exemplary vapor generation system 100 of the present disclosure, comprising a proximal end 120 and a distal end 122, and defining a lumen 124 therethrough extending from proximal end 120 to distal end 122. Proximal end 120 of second outlet conduit 118 is configured to receive the positive air flow generated by air flow generator 104 and passing through first outlet conduit 110, whereby the positive air flow is directed out of distal end 122 of second outlet conduit 118 within tank 102, such as shown in FIG. 1.

Figure 2:
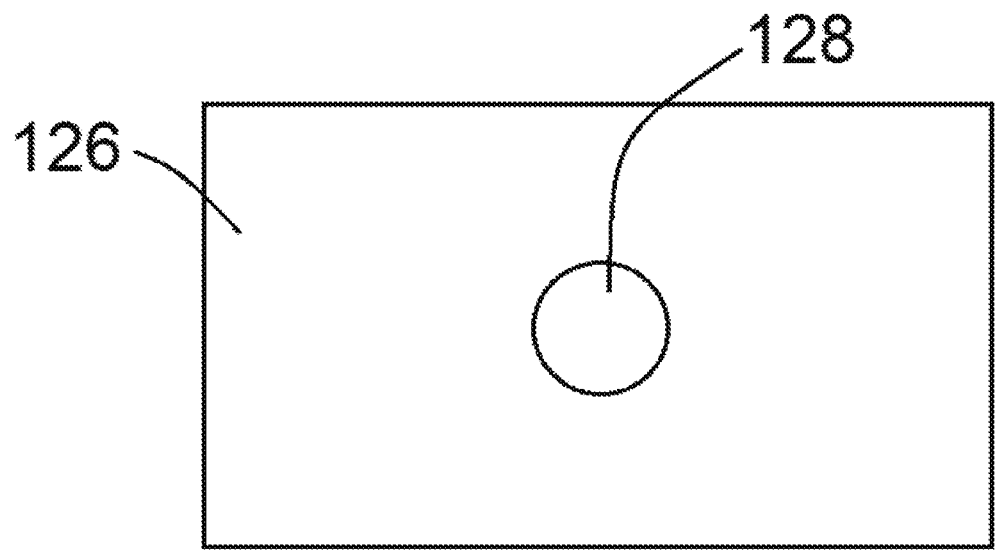
FIG. 2 shows a lid configured for placement upon a tank, according to an exemplary embodiment of the present disclosure.
Figure 3:
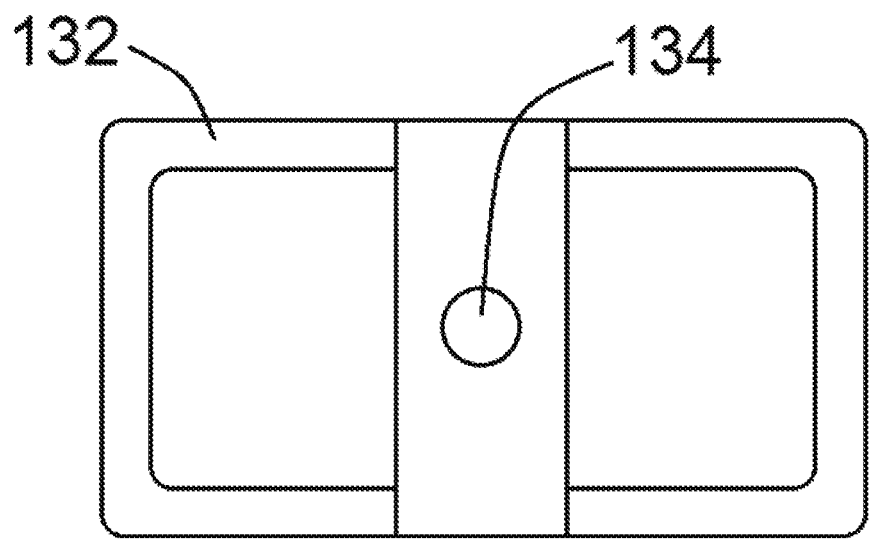
FIG. 3 shows a flotation element for use within a tank, according to an exemplary embodiment of the present disclosure.

In various embodiments, a lid 126 may be positioned relative to or otherwise attached to tank 102, such as shown in FIG. 1, defining an aperture 128 therein/therethrough, such as shown in FIG. 2, whereby second outlet conduit 118 passes into tank 102. Within tank 102, such as shown in FIG. 1, second outlet conduit 118 can be coupled to flotation element 132, such as a device known or developed in the art configured to float on the surface of liquid chemical 150, via, for example, a second conduit attachment 130, such as a bracket or other device known or developed in the art configured to connect second outlet conduit 118 to flotation element 132. Flotation element 132 has an aperture 134 defined therein/therethrough, such as shown in FIG. 3, whereby the positive air flow generated by air flow generator 104 is ultimately directed out of distal end 122 of second outlet conduit 118 and down onto the surface of liquid chemical 150.

As shown in FIG. 1, vapor generation system 100 also comprises a means for volatilized/vaporized chemical to exit from tank 102. In at least one embodiment, such as shown in FIG. 1, tank 102 further defines a tank aperture 160, configured so that volatilized/vaporized chemical from within tank 102 can exit tank 102. In at least another embodiment, such as shown in FIG. 4, lid 126 comprises a second lid aperture 128 defined therein/therethrough, so that one lid aperture 128 can receive part of second outlet conduit 118, for example, and another lid aperture 128 can be used so that volatilized/vaporized chemical can exit tank 102. The exemplary embodiment of vapor generation system 100 shown in FIG. 4 has a flotation element 132 with a relatively smaller cross-sectional area than that shown in FIG. 1. Flotation elements 132 may be configured as platforms, such as shown in FIG. 3.

Flotation elements 132, such as shown in FIGS. 1 and 4, contact chemical 150 and are positioned relative to a surface 152 of liquid chemical. As shown in FIGS. 1 and 4, part of flotation element 132 may be submerged within chemical 150 (below/within surface 152).

Figure 5:
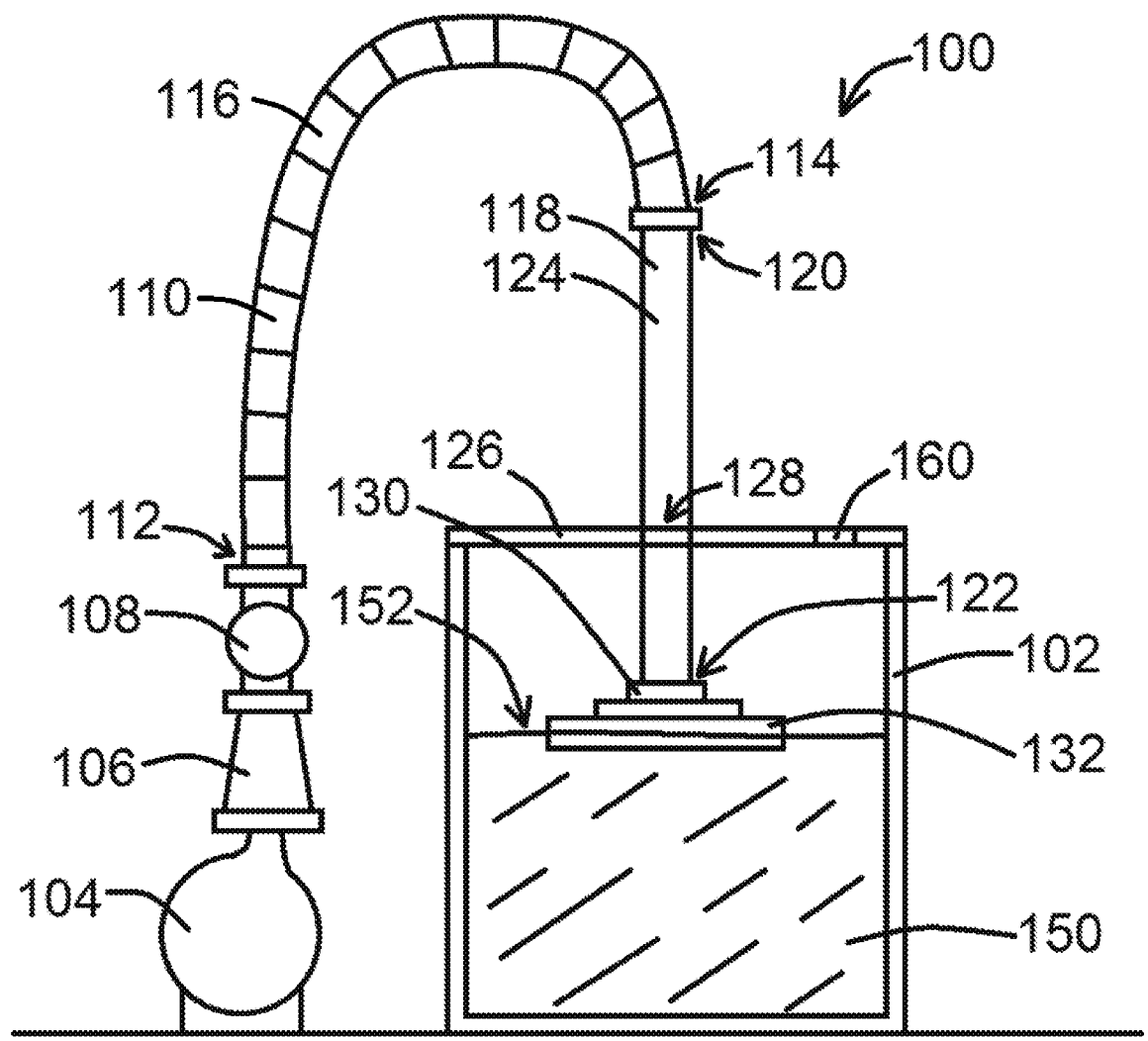
FIG. 5 shows components of a vapor generation system having a tank with more liquid chemical therein as compared to FIG. 4, according to an exemplary embodiment of the present disclosure.

FIG. 5 shows the embodiment of vapor generation system 100 shown in FIG. 4, but in a relative position when there is more chemical 150 in tank 102 than shown in FIG. 4. For example, when an initial quantity of chemical 150 is positioned within tank 102, such as shown in FIG. 5, flotation element 132 is relatively higher within tank 102 as the surface 152 of chemical 150 is higher within tank 102. As chemical 150 volatilizes/vaporizes over time, surface 152 drops as the quantity of liquid chemical 150 within tank 102 drops (and whereby volatilized/vaporized chemical exits tank 102 and is, for example, ultimately distributed at or near a landfill or as otherwise distributed and/or collected/stored as may be desired.

Figure 6:
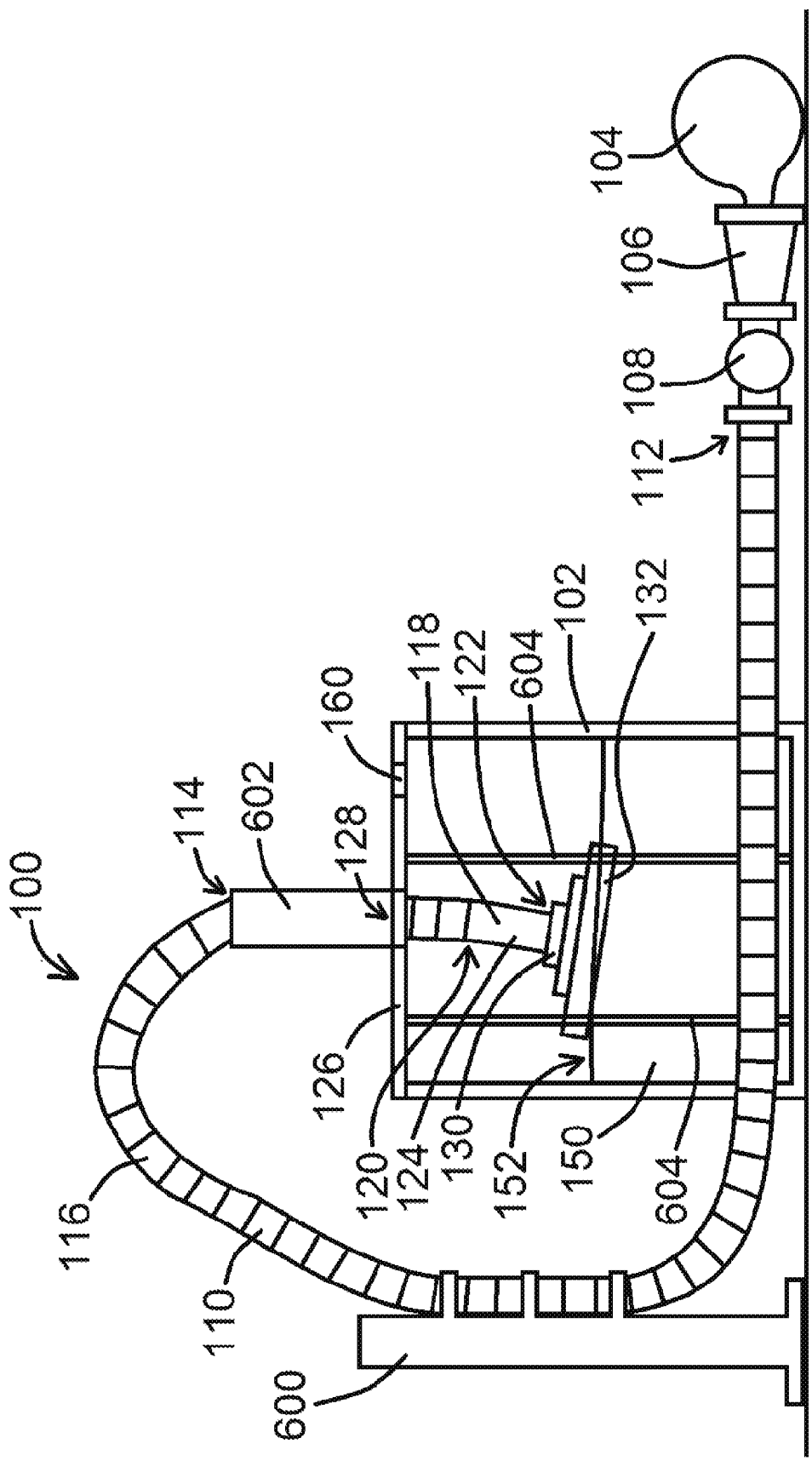
FIG. 6 shows components of a vapor generation system having a relatively long first outlet conduit as compared to FIG. 4, according to an exemplary embodiment of the present disclosure.

FIG. 6 shows an additional exemplary embodiment of a vapor generation system 100 of the present disclosure. As shown in FIG. 6, vapor generation system 100 has several of the same components/features as shown in FIG. 4, but utilized in a different configuration. As shown in FIG. 6, vapor generation system 100 utilizes a longer first outlet conduit 110 supported by a stand 600 allowing first outlet conduit 110 to bend in an appropriate arc to allow it to pass down into tank 102. As shown in FIG. 6, a rigid tube 602, such as a pipe or other device known or developed in the art, is affixed to or otherwise positioned at the top of tank 102 or lid 126 through which first outlet conduit 110 enters into tank 102 through aperture 128 or aperture 160. In this exemplary embodiment of vapor generation system 100, rigid tube 602 helps ensure horizontal stability of first outlet conduit 110 in tank 102 by maintaining tension on first outlet conduit 110 and/or providing a path to guide first outlet conduit 110 into tank 102. Within tank 102, first outlet conduit 110 may be attached to a short second outlet conduit 118, such as shown in FIG. 6, which is coupled to a flotation element 132, or first outlet conduit may be directly coupled to flotation element 132. Flotation element 132 is supported by one, two, three, four, or more guide rods 604 to help ensure horizontal stability of flotation element 132. However, in spite of the support provided by guide rods 604 and rigid tube 602, due to the flexibility of first outlet conduit 110, the surface tension disruption of surface 152 of liquid chemical 150 caused by the positive air flow passing through second outlet conduit 118 can result in a canted/angled positioning of flotation element 132 within tank 102, thus compromising the consistency of the volatilization of surface 152 of liquid chemical 150. The vapor generation system 100 embodiment shown in FIG. 1 may then be viewed as advantageous as compared to the embodiment shown in FIG. 6, as the embodiment shown in FIG. 1 has a longer second conduit 118 comprised of a rigid material, resulting in reduced lateral movement within tank 102 without the necessity of rigid tube 602. The embodiment of vapor generation system 100 shown in FIG. 1 also has a wider flotation element 132, which is able to obtain and maintain horizontal stability without the necessity of guide rods 604. It is noted that by changing the length of second outlet conduit 118 and changing the width of flotation element 132, vapor generation system 100 as shown in FIG. 1 (as compared to FIG. 6) can obtain better horizontal stability of flotation element 132 which results in even air flow through second outlet conduit 118 onto surface 152 of liquid chemical 150 and, ultimately, more uniform vapor generation.

Figure 7:
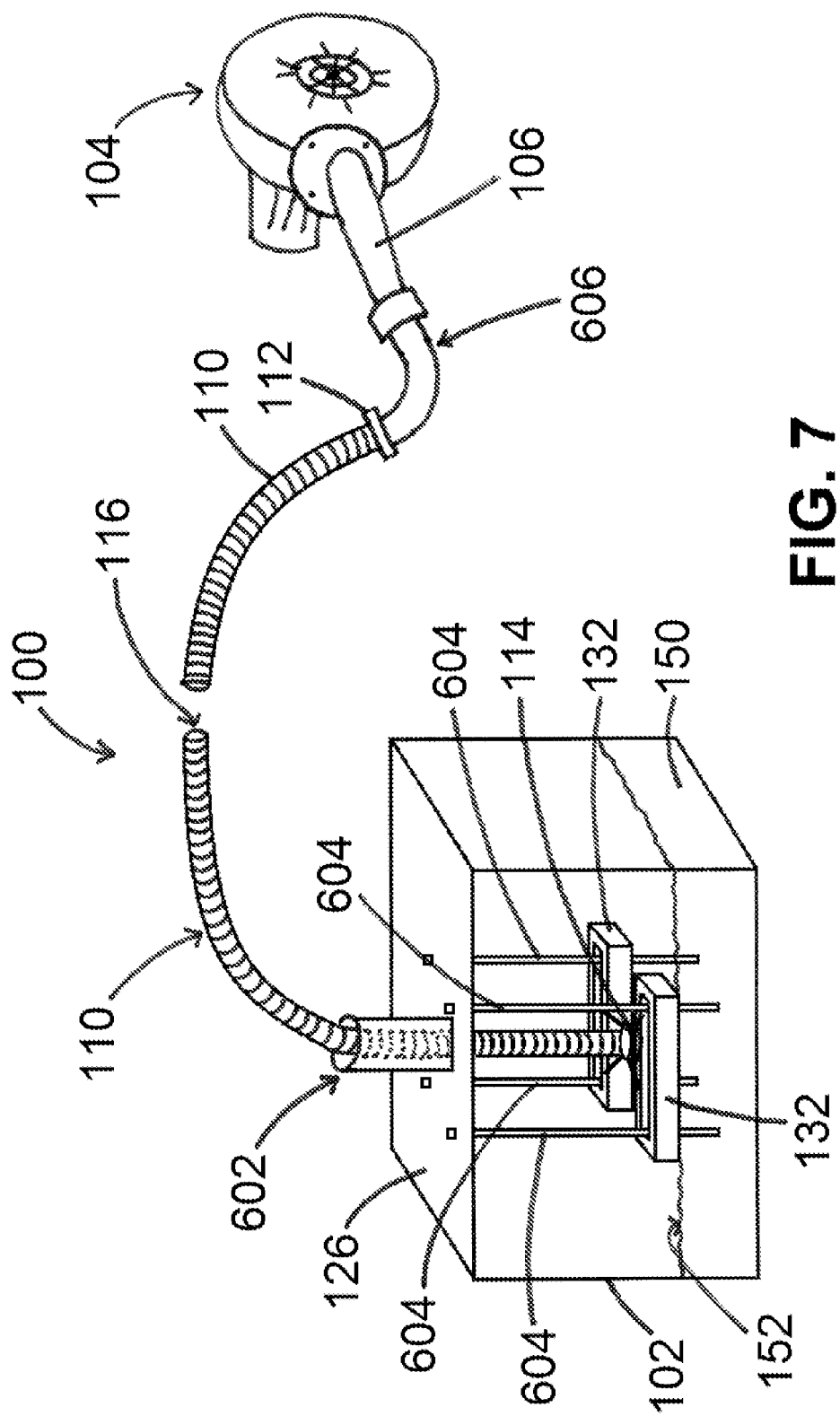
FIG. 7 shows components of a vapor generation system having a relatively shorter first outlet conduit, an elbow joint and no stand as compared to FIG. 6, according to an exemplary embodiment of the present disclosure.

FIG. 7 shows an additional exemplary embodiment of a vapor generation system 100 of the present disclosure. As shown in FIG. 7, vapor generation system 100 has several of the same components/features as shown in FIG. 6, but does not have an air flow velocity controller 108 or stand 600. As shown in FIG. 7, vapor generation system 100 does not have a second outlet conduit 118. Rather, vapor generation system 100 utilizes a longer first outlet conduit 110 coupled directly to mating flange 106 via an elbow joint 606 as shown in FIG. 7. In this exemplary embodiment of vapor generation system 100, in the absence of a stand 600, elbow joint 606 is insufficient to ensure proper tension on first outlet conduit 110 thus compromising horizontal stability of first outlet conduit 110 and flotation element 132 within tank 102. Further, the absence of a rigid second outlet conduit 118 and the flexible nature of first outlet conduit 110 can result in undesired movement of first outlet conduit 110 and corresponding canted/angled positioning of flotation element 132 within tank 102, thus compromising the consistency of the volatilization of surface 152 of liquid chemical 150. The vapor generation system 100 embodiment shown in FIG. 6 may then be viewed as advantageous as compared to the embodiment shown in FIG. 7, as the embodiment shown in FIG. 6 has components in place to improve the horizontal stability, specifically, stand 600 and second outlet conduit 118. It is noted that by improving the horizontal stability of flotation element 132, vapor generation system 100 as shown in FIG. 6 (as compared to FIG. 7) can obtain more even air flow through second outlet conduit 118 onto surface 152 of liquid chemical 150 and, ultimately, more uniform vapor generation.

Figure 8:
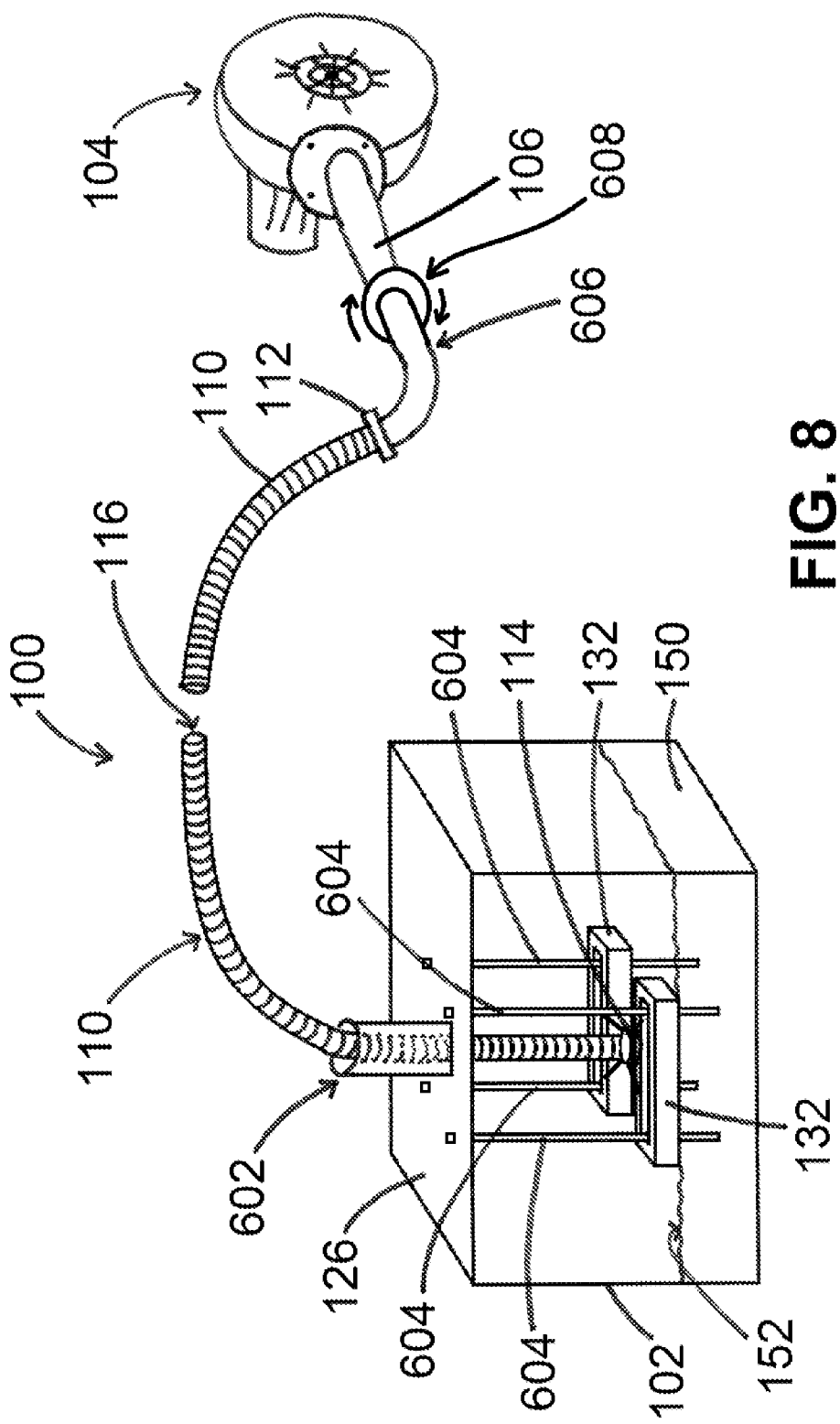
FIG. 8 shows components of a vapor generation system having a bearing coupled to an elbow joint as compared to FIG. 7, according to an exemplary embodiment of the present disclosure.

FIG. 8 shows an additional exemplary embodiment of a vapor generation system 100 of the present disclosure. As shown in FIG. 8, vapor generation system 100 has several of the same components/features as shown in FIG. 7, but also has an additional element, bearing 608. In this embodiment, as shown in FIG. 8, elbow joint 606 is coupled to bearing 608 to allow for the articulation of first outlet conduit 110 as vertical movement of first outlet conduit 110 occurs within tank 102. However, as it was determined that bearing 608, as shown in FIG. 8, was unnecessary because the flexible nature of first outlet conduit 110 allowed for sufficient vertical movement within tank 102, future iterations of vapor generation system 100 did not include bearing 608. The vapor generation system 100 embodiment shown in FIG. 7 may then be viewed as advantageous as compared to the embodiment shown in FIG. 8, as the embodiment shown in FIG. 7 does not have the unnecessary bearing 608 thus reducing production costs.

Figure 9:
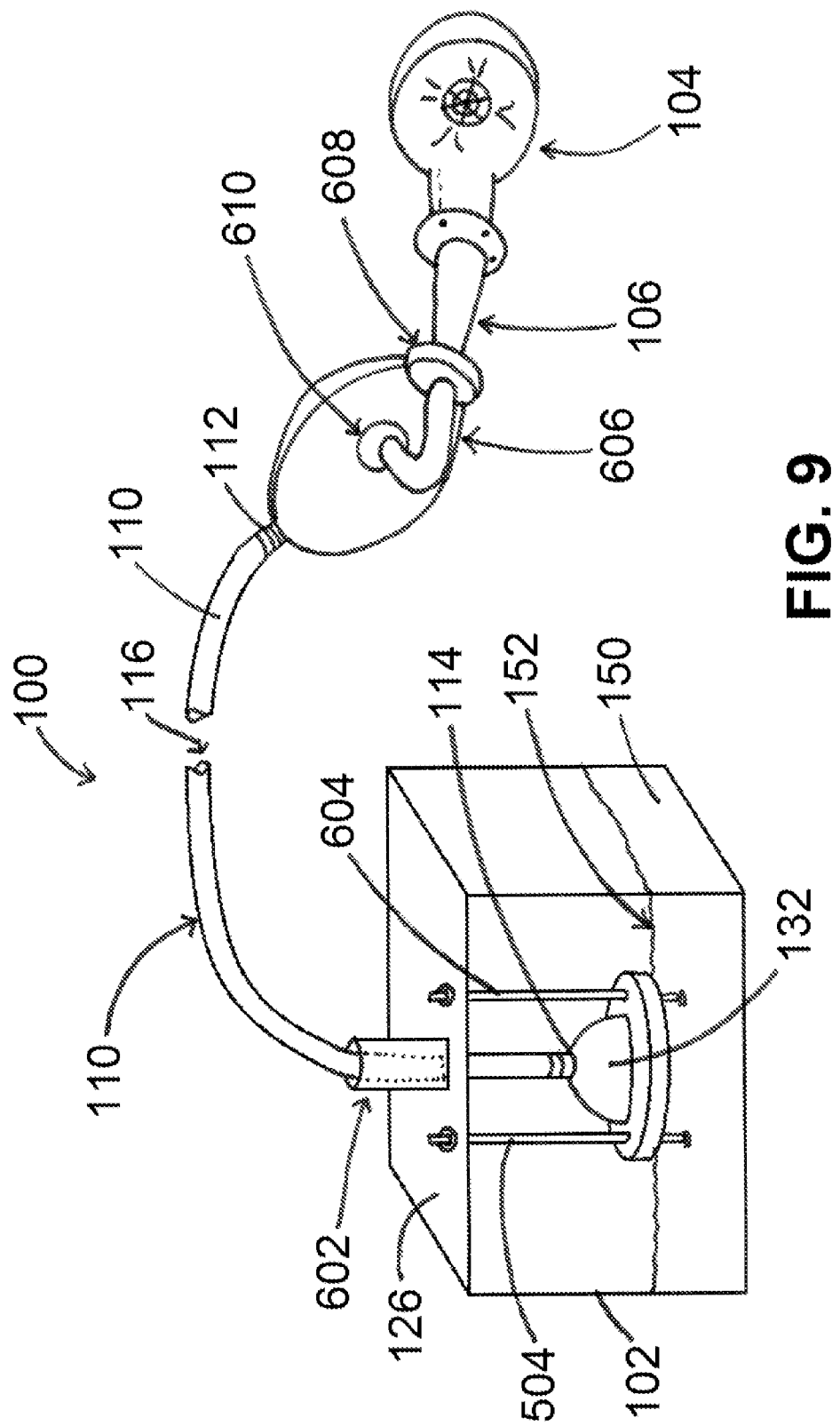
FIG. 9 shows components of a vapor generation system having an air channeling device, thinner first outlet conduit and different shaped flotation element as compared to FIG. 8, according to an exemplary embodiment of the present disclosure.

FIG. 9 shows an additional exemplary embodiment of a vapor generation system 100 of the present disclosure. As shown in FIG. 9, vapor generation system 100 has several of the same components/features as shown in FIG. 8, but also has an additional bearing 608 coupled to air channeling device 610, such as a device known or developed in the art to allow for the channeling of the flow of air generated by air flow generator 104 through it to first outlet conduit 110. As shown in FIG. 9, in this exemplary embodiment of a vapor generation system 100, the proximal end 112 of first outlet conduit 110 is coupled to air channeling device 610 while distal end 114 of first outlet conduit 110 is coupled to a flotation element 132. In the exemplary embodiment shown in FIG. 9, first outlet conduit 110 is comprised of a less flexible material than as shown in FIG. 8, FIG. 7, FIG. 6, FIG. 4 and FIG. 1. Further, in this exemplary embodiment, flotation element 132 is secured by only two (2) guide rods 604, as shown in FIG. 9. As it was eventually determined that air channeling device 610, as shown in FIG. 9, resulted in an undesirable loss in air flow pressure into first outlet conduit 110, future iterations of vapor generation system 100 did not include air channeling device 610. Further, as it was eventually determined that a more flexible first outlet conduit 110 and additional guide rods 604, as shown in FIG. 8, were necessary to maintain the horizontal stability of flotation element 132 within tank 102, the exemplary embodiment of vapor generation system 100 represented in FIG. 9 was deemed less effective. The vapor generation system 100 embodiment shown in FIG. 8 may then be viewed as advantageous as compared to the embodiment shown in FIG. 9 as its components contributed to better horizontal stability of flotation element 132 which results in more even air flow through first outlet conduit 110 onto surface 152 of liquid chemical 150, and, ultimately, more uniform vapor production.

As referenced herein, the generation of chemical vapor from liquid chemical 150 is performed using exemplary vapor generation systems 100 of the present disclosure. By way of various embodiment testing, it has been determined that depending on overall configuration (dimensions, power, etc.) of an exemplary vapor generation system 100 of the present disclosure, a particular distance from a distal end 114, a distal end 122, a second conduit attachment 130, a flotation element 132, etc., referring to the general exit aperture/location of air from within a first outlet conduit 110 or a second outlet conduit 118, for example, into tank 102 to strike surface 152 of liquid chemical 150, is important to overall volatility/vaporization of liquid chemical 150. Phrased differently, a particular distance of air exiting a particular duct/conduit of system 100 to a surface 152 of liquid chemical 150 has been identified as an important factor with respect to overall efficient and effective operation of an exemplary vapor generation system 100 of the present disclosure. In view of the same, the various vapor generation system embodiments shown and referenced herein are configured so that said distance can be established and maintained over time while the amount of liquid chemical 150 within tank 102 changes due to volatilization/vaporization.

Figure 10:
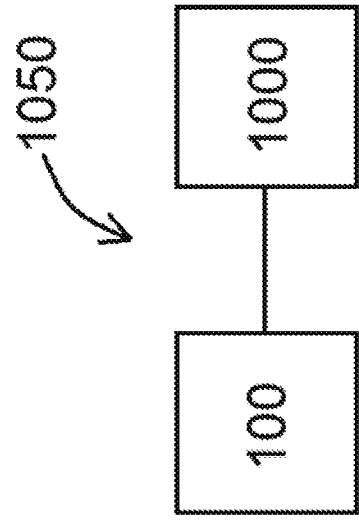
FIG. 10 shows a block component diagram of an overall system, according to an exemplary embodiment of the present disclosure.
Figure 11:
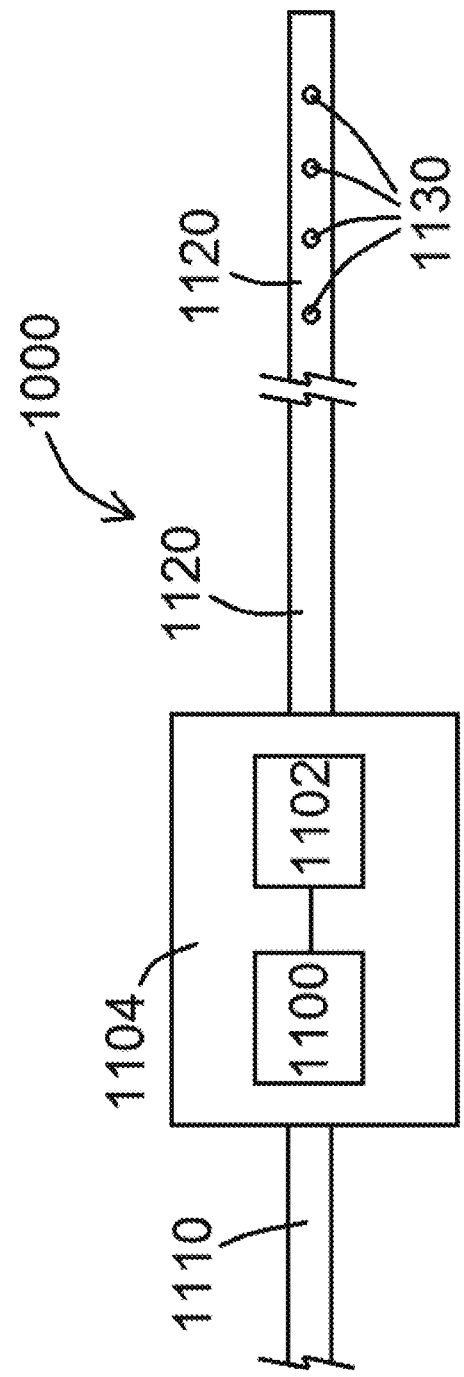
FIGS. 11 and 12 show components of a vapor distribution system, according to exemplary embodiments of the present disclosure.

FIG. 10 shows an exemplary vapor distribution system 1000 of the present disclosure as a component of a block component diagram. An exemplary vapor distribution system 1000 of the present disclosure, along with an exemplary vapor generation system 100 of the present disclosure, may be referred to as an overall system 1050, as shown in FIG. 10. FIG. 11 shows components of an exemplary vapor distribution system 1000 of the present disclosure. As shown in FIG. 11, an exemplary vapor distribution system 1000 of the present disclosure comprises an air flow generator 1100, such as a fan, operably coupled to a motor 1102 configured to operate air flow generator 1100. Air flow generator 1100 and/or motor 1102 may be positioned within housing 1104 (or in separate housings 1104, depending on embodiment).

In at least one embodiment, vapor distribution system 1000 comprises (or is operably coupled to) an inlet conduit 1110, used to connect an exemplary vapor generation system 100 directly or indirectly to vapor distribution system 1000. Additional conduits (which may also be referred to as inlet conduits 1110) may also be used, such that two or more inlet conduits may be used to connect vapor generation system 100 directly or indirectly to vapor distribution system 1000. Inlet conduit 1110 may couple to housing 1104, either directly or indirectly, and may also couple to vapor generation system 100 at aperture 160, for example, so that vapor generated using vapor generation system 100 exits aperture 160 and is provided to or received by vapor distribution system 1000. Inlet conduit 1110 may be considered as part of a vapor distribution system 1000 or as part of a vapor generation system 100 of the present disclosure. Exemplary vapor distribution systems 1000 of the present disclosure, such as shown in FIG. 11, may also comprise (or be operably coupled to) one or more distribution conduits 1120. At least one of the one or more distribution conduits 1120 have one or more, and generally a plurality, of apertures 1130 defined therethrough so that vapor generated using an exemplary vapor generation system 100 of the present disclosure can be forced through portions of vapor distribution system 1000 and out of the one or more apertures 1130 and generally into the atmosphere. Such an overall system 1050 may be used to, for example, generate vapor used to neutralize noxious or otherwise offensive odors present in the atmosphere, such as at or near a landfill, farm, and/or other industrial/commercial location that generates said noxious or otherwise offensive odors.

Figure 12:
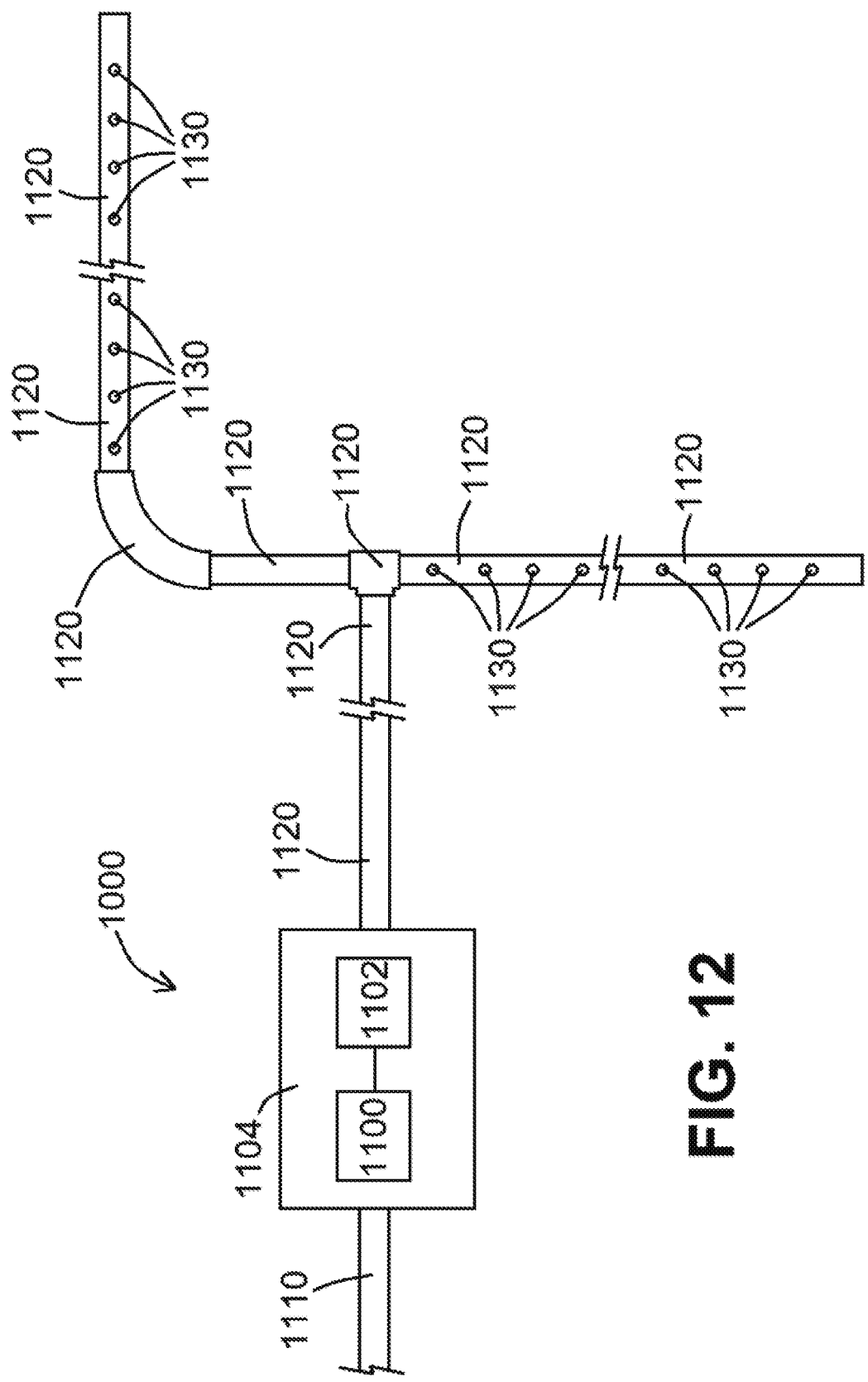
Figure 13:
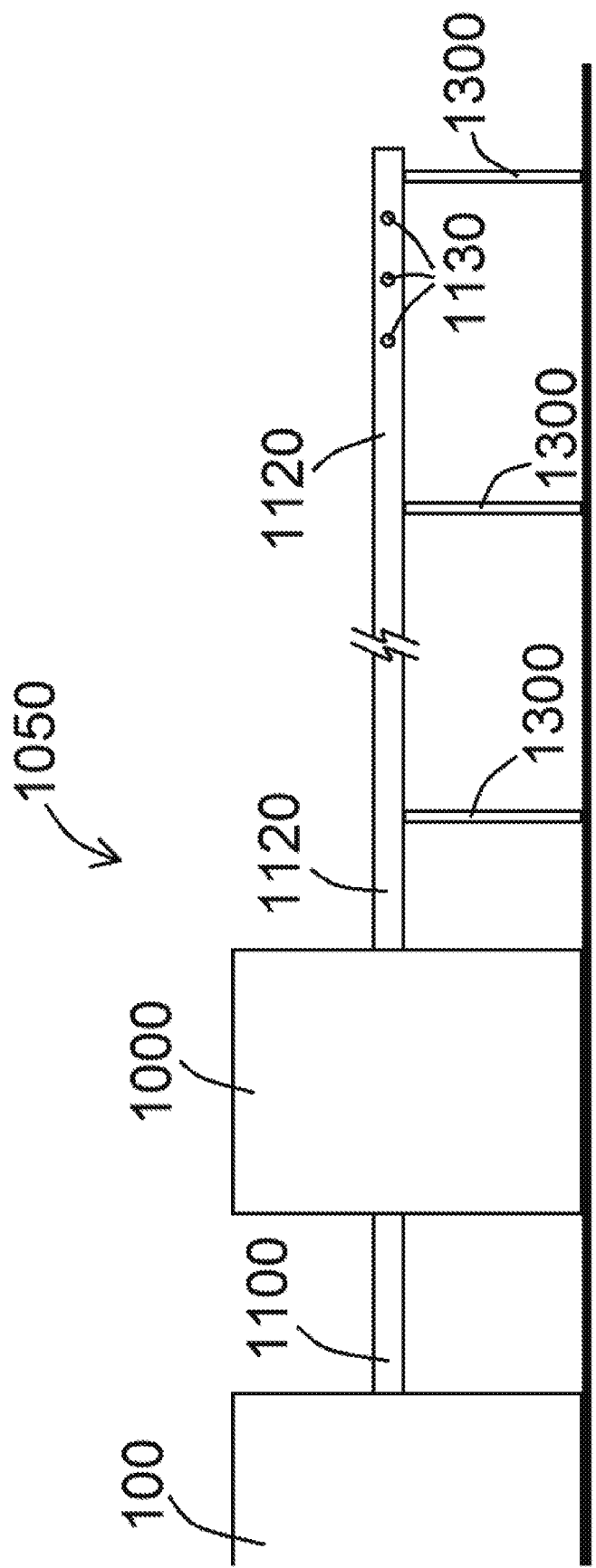
FIG. 13 shows a side view of an overall system, according to an exemplary embodiment of the present disclosure.

FIG. 12 shows an exemplary vapor distribution system 1000 having multiple distribution conduits 1120. As shown therein, distribution conduits 1120 may be straight, curved, bent, etc., and may have any number of apertures 1130 defined therein. Further, distribution conduits 1120 may have any number of dimensions so that said distribution conduits 1120 are configured for a particular vapor distribution purpose, as provided in further detail below.

While distribution of vapor using a vapor distribution system 1000 of the present disclosure may appear to be straightforward, the overall process is wrought with pitfalls which must be addressed, several of which due to improper assumptions made with respect to the science of air movement and air measurement. An important element is the selection/sizing of an appropriate air flow generator 1100 and/or motor 1102 (alone or in combination) in order to properly and effectively distribute vapor. Field testing of embodiments of vapor distribution systems 1000 of the present disclosure concluded that a minimum velocity of vapor exiting one or more distribution conduits 1120 into the atmosphere must be established. Too little velocity implies that the vapor is merely "trickling" out of the various apertures 1130 and therefore not effectively dispersing into the surrounding atmosphere. So for the chemical vapor to be most effective (with respect to atmospheric distribution), it must have time and space within which to contact and react with malodors (noxious or otherwise offensive odors). Such a minimum threshold, for example, may be 25 mph per aperture 1130, based on field testing.

Prior art distribution systems rely/depend on one single fan used to both generate vapor and distribute vapor. In known systems where multiple fans are used, it is noted that due to configurations and other mechanical restraints of said systems, relatively large diameter (6" to 8" diameter) pipe is required to distribute chemical vapor. Conversely, various vapor distribution systems 1000 of the present disclosure, configured with particular motor 1102 power and air flow generator 1100 size/configuration, can properly and effectively disperse vapor into the surrounding atmosphere using, for example, 4" diameter distribution conduit 1120 having a length of 2000' or more. Being able to effectively distribute vapor using a 4" diameter distribution conduit 1120 versus a 6" or 8" diameter pipe results in a significant cost savings, not just for the distribution conduit 1120 alone, but also due to the unintended consequences such as overall higher weight of the pipe and the concomitant infrastructure required to support said weight. It is noted that elevating distribution conduit 1120 off of the ground results in superior vapor distribution as compared to having distribution conduit 1120 positioned on the ground, as depicted in the side view of an exemplary overall system 1050 shown in FIG. 13 whereby a series of stands 1300 are used to maintain some or all of distribution conduit 1120 above the ground. A smaller distribution conduit 1120 results in less weight, and therefore fewer or smaller stands 1300 can be used to maintain the distribution conduit 1120 above the ground, noting that attempting to elevate 6" or 8" diameter pipe above the ground, such as in 1000', 2000', or larger or smaller sections, may/could be cost prohibitive.

Figure 18:
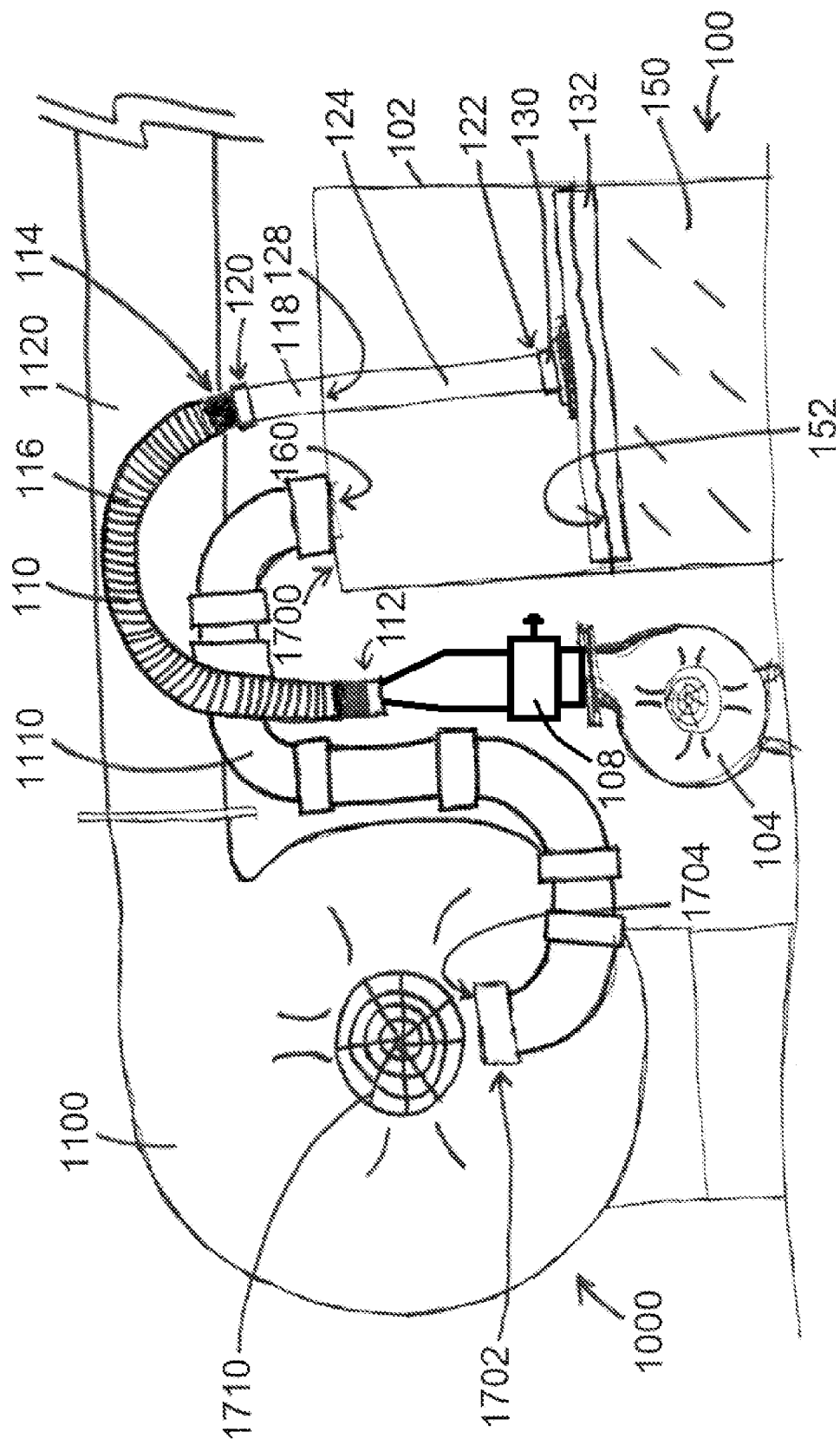
Figure 19:
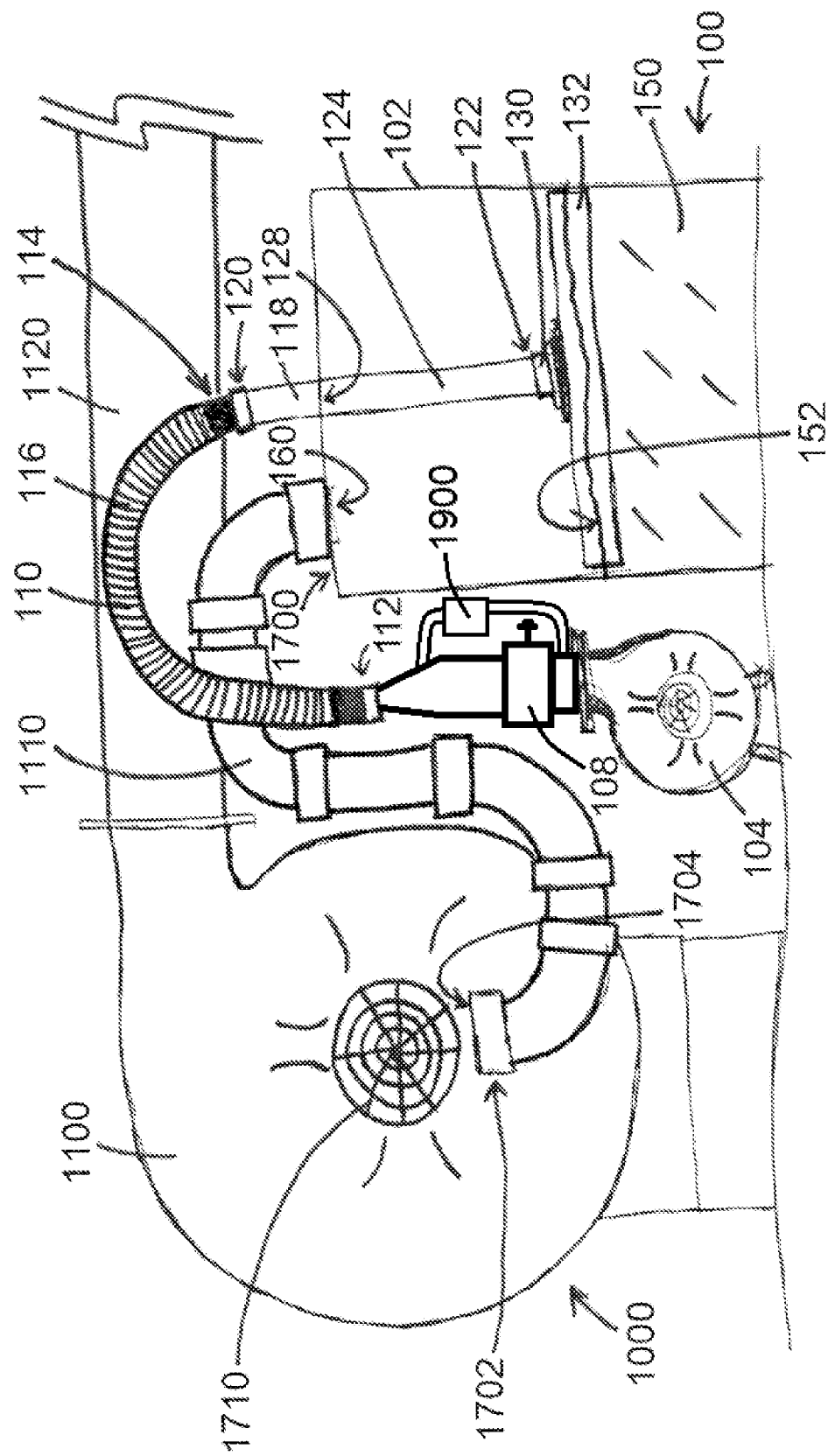

A primary shortfall of using a single fan to generate and distribute vapor, as compared to Applicant's use of air flow generator 104 (within vapor generation system 100) and air flow generator 1100 (within vapor distribution system 1000), is that both the output and the generation of vapor are dependent upon variables that are often mutually exclusive. For example, the velocity of air striking a surface 152 of liquid chemical 150 within tank 102 is likely different than the velocity of air necessary to move chemical vapor through distribution conduit(s) 1120 and therefore at odds with one another. By using a vapor generation system 100 and a vapor distribution system 1000 of the present disclosure, each system 100, 1000 can be specifically regulated and configured as desired, taking Bernoulli's principles and the law of conservation of energy, for example, into account.

Prior art systems drastically overestimate the cubic feet per minute (CFM) necessary to move the vapor through distribution pipes, and generally underestimate the necessary static pressure required to move vapor through said distribution pipes. One system in particular bases its fan sizing determination on horsepower, which generally does not make sense, as horsepower should only be considered after the correct size and shape of air flow generator 104, such as a fan, has been identified. An appropriate fan (air flow generator 104, 1100) size and shape are a direct function of the CFM and static pressure required for a given length of pipe, such as one or more distribution conduits 1120. The horsepower required to turn the identified fan is then determined by the manufacturer of the air flow generator 104, 1100. If the fan (air flow generator 1100, for example) and motor 1102 (if separate from air flow generator 1100, noting that air flow generators 104, 1100 of the present disclosure may comprise a fan or a fan and a motor, such as a motor 1102) were based solely on horsepower, such as 10 hp and 1600 CFM, an excessive amount of air flow would be generated, preventing proper laminar flow through the pipe (such as distribution conduit 1120), and instead generating extreme turbulence which results in highly decreased and volatile static pressure, as well as significant backpressure into housing 1104 and potentially back into tank 102 of vapor generation system 100. Prior art systems generally use excessive horsepower, such that the turbulence and back pressure cause significant inefficiencies, whereas a properly sized airflow generator 1100 and motor 1102, given a particular length and dimension of distribution conduit 1120, would result in a highly effective and efficient overall system 1050, as generally described herein.

Ultimate delivery of vapor via apertures 1130, using an efficient and effective vapor distribution system 1000, is one goal of the present disclosure. Considering a stadium analogy, say a stadium can hold 40,000 people, but it has only one door. No matter how hard the crowd would push, there is only one number of people that can fit through the door at any given time. An inefficient system, such as prior art systems using excessive horsepower motors, excessively large fans, etc., cause so much air flow that cannot make it out of the given number of openings, so that turbulence and backflow is the norm, rather than proper laminar flow. Applicant's present disclosure of systems 100, 1000, 1050 effectively address these problems.

The appropriate approach is to initially determine the overall length of distribution conduit 1120 desired for a particular purpose, the number of apertures 1130 desired or needed, and the overall size (diameter) of said distribution conduit 1120. A model/working prototype can then be constructed based on said dimensions, which, using the laws of physics, can forecast the overall parameters of air flow generator 1100 and/or motor 1102 needed to achieve the desired vapor distribution.

An additional embodiment of an overall system 1050 of the present disclosure is shown in FIG. 16. As shown therein, a vapor generation system 100 of the present disclosure is operably coupled to a vapor distribution system 1000 of the present disclosure, with various componentry/features as previously described. In at least this embodiment, a controlled and measurable volatilization/vaporization of liquid chemical 150 can be had, which, in at least this embodiment, requires that the airflow into tank 102, as generated by air flow generator 104, has a discharge capability (via aperture 160) equal or greater to the intake capacity, for example, 5 cubic feet per minute (CFM) of air flow into tank 102 must allow for 5 CFM or greater air flow (of volatilized/vaporized chemical) out of aperture 160. FIG. 16 shows an exemplary embodiment for discharging the volatilized/vaporized chemical, whereby the inlet conduit 1100 was relatively narrow (having a relatively small diameter, for example), and therefore could not successfully balance the incoming CFM with the vented/discharged CFM. In attempt to correct for this, and by increasing the size of aperture 160 of tank 102, such as to a diameter of 3 inches in at least one embodiment, the flow of air into tank 102 from air flow generator 104 was balanced with the outgoing flow of volatilized/vaporized chemical out of aperture 160, allowing for the rate of volatilization to be controllable and measurable by, for example, adjusting air flow velocity controller 108 to adjust the flow of air from air flow generator 104 into tank 102, such as shown in FIG. 17. FIG. 17 shows an exemplary overall system 1050 of the present disclosure, whereby aperture 160 of tank 102 is larger than aperture 160 shown in FIG. 16, allowing for a larger inlet conduit 1110 to be used. Inlet conduit 1110, as shown in FIG. 17 for example, has a proximal end 1700 and a distal end 1702 defining a distal opening 1704. Distal end 1702, and therefore distal opening 1704, can then be positioned adjacent to, but not actually coupled to, an inlet 1710 of air flow generator 1100, so that volatilized/vaporized chemical can exit tank 102 via aperture 160, travel through inlet conduit 1110, and escape from distal opening 1704, whereby some or all of the volatilized/vaporized chemical that escapes from distal opening 1704 would enter into inlet 1710 by way of suction/vacuum, as air flow generator 1100, in operation, would effectively suck in air, and/or volatilized/vaporized chemical that may be present in the vicinity of inlet 1710, so that it can ultimately escape air flow generator 1100 via aperture(s) 1130 of distribution conduit(s) 1120.

Upon identifying how to control the rate of vaporization, the discovery was made that the air flow velocity controller 108 (also referred to as an attenuating device, which may be, for example, a ball valve) must be, in at least some overall system 1050 embodiments, sufficiently flexible to allow for subtle adjustments to air flow. As such, an air flow velocity controller 108 other than a ball valve was tested, namely an air flow velocity controller 108 being/configured as a gate valve, to allow for greater precision regarding adjustment of air flow, such as shown in FIG. 18. Additional precision was capable by way of connecting a gauge 1900 to vapor generation system 100, such as shown in FIG. 19, whereby gauge 1900 is configured to measure, for example, inches of water column, which is a method for measuring static pressure. Feedback from gauge 1900 allows a user of vapor generation system 100 to more precisely adjust air flow velocity controller 108 to obtain desired air flow through vapor generation system 100. By metering air flow prior to and after air flow velocity controller 108, a reading of X inches of water column, for example, can be correlated within Y units of vapor production from vapor generation system 100. Accordingly, and in at least one embodiment, gauge 1900 is connected to portions of vapor generation system 100 proximal to and distal to air flow velocity controller 108. In at least other embodiments, gauge 1900 is connected to portions of vapor generation system 100 proximal or distal to air flow reducer 106.

FIGS. 20A-20D show various views of an exemplary flotation element 132 of the present disclosure. Via performance of various tests of various vapor generation system 100 embodiments, it was observed that air flow directed vertically onto the surface 152 of liquid chemical 150, irrespective of velocity, could result in less controllable and/or less efficient vaporization/volatilization of chemical 150. In view of the same, additional flotation element 132 embodiments, also referred to herein as diffusers, were designed and configured so that they redirect vertical flowing air into a laminar horizontal flow of air across a broader surface area of liquid chemical 150, which in at least some embodiments, resulted in more controllable and efficient vaporization/volatilization of chemical 150. As shown in one or more of FIG. 20A, exemplary flotation elements 132 comprise an inlet portion 2000 defining an inlet aperture 2002 therein, a first outlet portion 2004 defining a first outlet aperture 2006 therein, and a second outlet portion 2008 defining a second outlet aperture 2010 therein. Air flow from air flow generator 104 would enter inlet aperture 2002 in a relative vertical direction, and be diverted to a horizontal/laminar flow direction within flotation element 132 and exit horizontally through first outlet aperture 2006 and second outlet aperture 2010. An internal lumen 2012, such as shown in FIG. 20C, would be defined within portions of inlet portion 2000, first outlet portion 2004, and second outlet portion 2008, in various embodiments.

Figure 21:
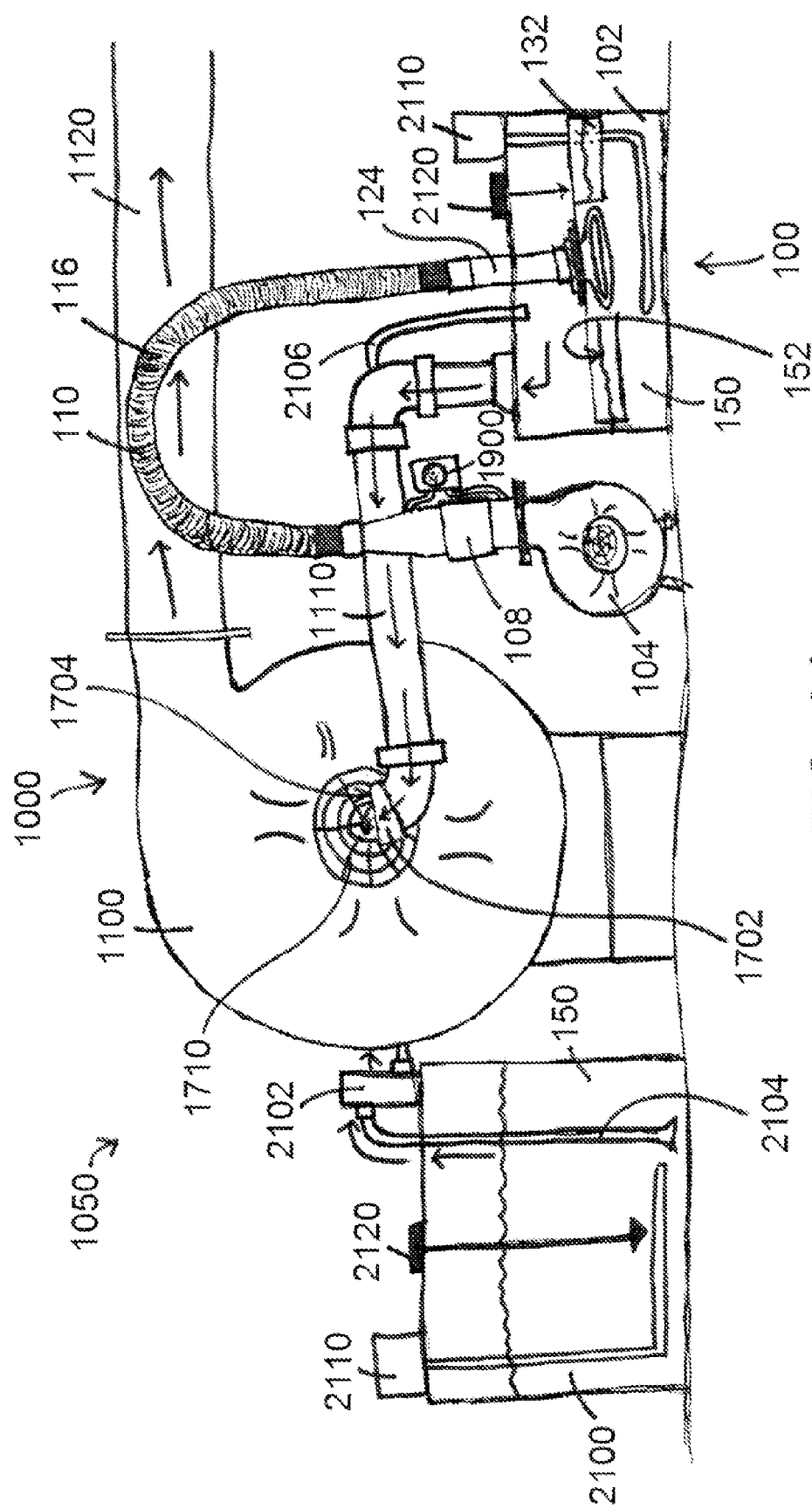

FIG. 21 shows components of an overall system 1050 of the present disclosure comprising a vapor generation system 100 and a vapor distribution system 1000, according to an exemplary embodiment of the present disclosure. Subsequent testing of the combination of a uniquely designed air diffuser (an exemplary air flow reducer 106 of the present disclosure) and a gate valve (an exemplary air flow velocity controller 108 of the present disclosure) revealed a flaw in a prototype design. Multiple tests revealed that, despite a balanced flow of air into and out of the evaporation tank (tank 102) at the beginning of the cycle, namely a full tank 102 of liquid chemical 150, as the level of liquid chemical 150 in tank 102 lessens due to evaporation (volatilization or vaporization of liquid chemical 150), static pressure of system 100 necessarily decreased. A lower static pressure implies an increase in air velocity traveling through the diffuser (air flow reducer 106) and therefore an increased level of production of volatilized/vaporized liquid chemical 150 as compared to the initial level of production at the full-tank amount. Therefore, it was discovered that either a constant adjustment to air flow within system 100 be made, namely to make static pressure constant by consistent gradual restriction of the gate valve (air flow velocity controller 108) or a method of keeping the level of liquid chemical 150 constant within tank 102 be engineered.

The choice was made to introduce a secondary feeder tank (an auxiliary feeder tank 2100) from which the product (liquid chemical 150) to be evaporated (volatilized/vaporized) is pumped out of auxiliary feeder tank 2100 and into the evaporation tank (tank 102) at a rate equal to or nearly equal to the rate of evaporation within tank 102. The desired rate of evaporation then becomes a function of static pressure as measured by inches of water column (using a static pressure gauge, which is an exemplary gauge 1900 of the present disclosure). To achieve the same, a pump 2102, such as shown in FIG. 21, can be used to pump liquid chemical 150 from auxiliary feeder tank 2100 to tank 102. A feeder tube 2104 coupled to pump 2102 can be used to withdraw/pump liquid chemical 150 from auxiliary feeder tank 2100 and into/through a pump distribution tube 2106 into tank 150. Phrased differently, pump 2102 can have a feeder tube 2104, and pump 2102 is configured to pump at least some of the liquid chemical 150 from auxiliary feeder tank 2100 through feeder tube 2104, through pump distribution tube 2106 coupled to pump 2102 or feeder tube 2104, and into tank 102.

In various system 100, 1000 embodiments, heaters 2110 can be used to increase the temperature of liquid chemical 150 within tank 102 and/or auxiliary tank 2100. Increasing the temperature of liquid chemical 150 within tank 102 and/or auxiliary tank 2100 can ultimately improve overall efficiency of systems 100, 1000 by facilitating volatilization/vaporization of liquid chemical 150 within tank 102 with less overall effort/energy. Heaters 2110 can be configured as immersion heaters 2110, as shown in FIG. 21, whereby portions of heaters 2110 are immersed within liquid chemical 150. Heaters 2110 can be positioned relative to tank 102 and/or auxiliary feeder tank 2100, as shown in FIG. 21. Overall levels of liquid chemical 150 within tank 102 and/or auxiliary feeder tank 2100 can be monitored using one or more level sensors 2120, as shown in FIG. 21. Level sensors 2120, in various embodiments, can be electronic point-to-point level sensors 2120, configured to obtain data relating to a level of first chemical 150 within tank 102 and/or auxiliary feeder tank 2100. Said data can be used to control operation of pump 2102, for example, as if a level of liquid chemical 150 falls below a desired level, pump 2102 can operate to pump liquid chemical 150 from auxiliary feeder tank 2100 into tank 102 as described above.

A further refinement was realized by replacing the gate-valve (an exemplary air flow velocity controller 108) with an iris damper (another exemplary air flow velocity controller 108). A gate-valve (exemplary air flow velocity controller 108) properly reduces or increases airflow depending on the user-defined setting. However, the change in airflow as the setting is adjusted is non-linear; for example, if one quarter-open is equal to 20 CFM, half open is equal to greater than 40 CFM. Therefore, an iris damper (exemplary air flow velocity controller 108) can be used in various system 100 embodiments, such as shown in FIG. 21, to replace the gate valve (another exemplary air flow velocity controller 108) for a considerably more linear rate of change when increasing or decreasing air flow (lower or higher static pressure) to achieve a desired level of evaporation (volatilization/vaporization of liquid chemical 150). The iris damper (exemplary air flow velocity controller 108) can therefore initially be calibrated to meet a desired evaporation rate, such as, for example, one inch of static pressure (as measured by the static pressure gauge 1900) being equal to 2.5 gallons of evaporated liquid chemical 150 (in an exemplary embodiment) and the level of liquid chemical 150 in the evaporation tank 102 is held constant vis-à-vis the constant transfer of liquid chemical 150 from the auxiliary feeder tank 2100.

Figure 14:
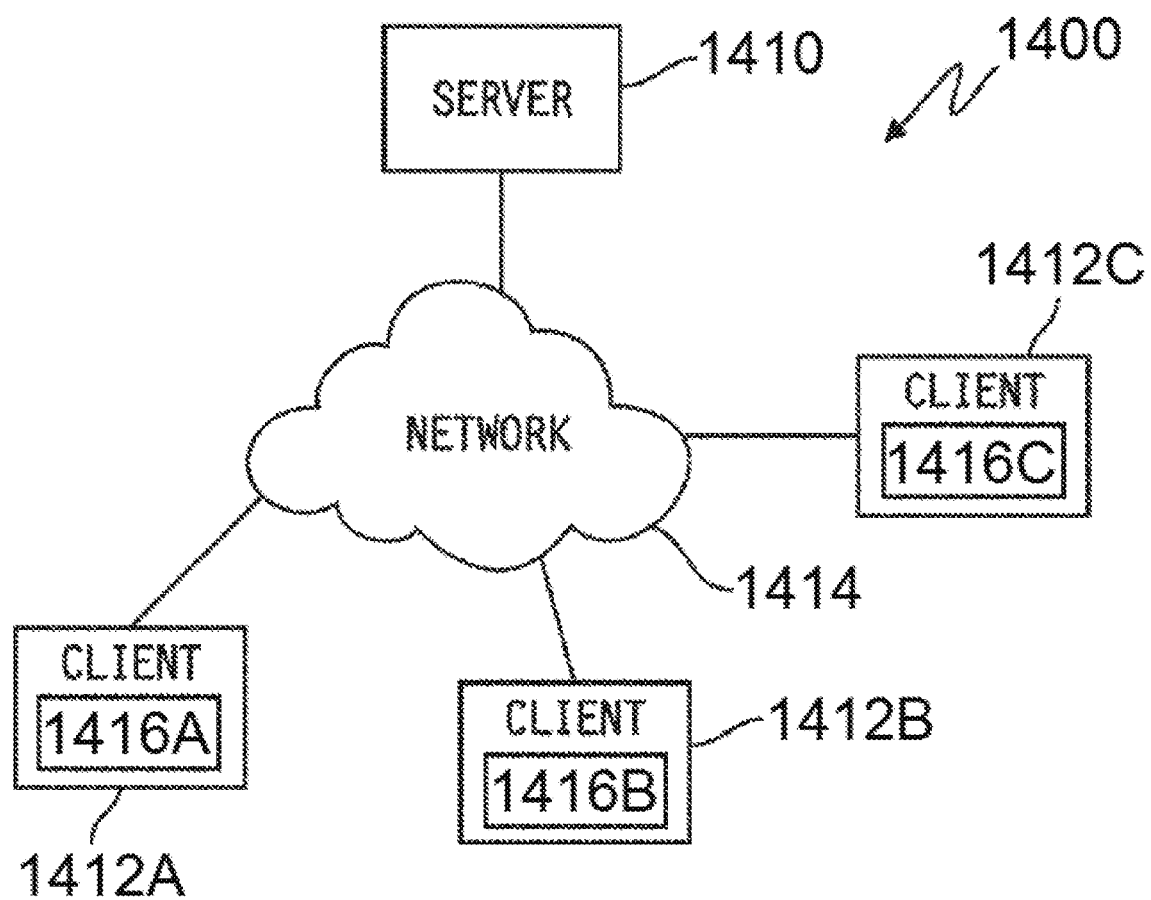
FIG. 14 shows a schematic diagrammatic view of a networked system in which embodiments of the present disclosure may be utilized, according to an exemplary embodiment of the present disclosure.

Various information/data from systems 100, 1000, 1050, such as levels of liquid chemical 150 within tank 102 and/or auxiliary feeder tank 2100 (such as detected using level sensor(s) 2120), temperatures of liquid chemical 150 within tank 102 and/or auxiliary feeder tank 2100 (such as obtained/facilitated using heater(s) 2110), level(s) of static pressure within system 100 (such as determined using gauge 1900), etc., can all be obtained and transmitted to one or more clients 1412A, 1412B, 1412C, such as through a network 1414, as shown in FIG. 14, and/or whereby various aspects of said information/data are stored in and/or are passed through the cloud (such that the system is "cloud-based." This allows for remote monitoring of systems 100, 1000, and 1050, allowing appropriate responsive action to be taken, such as adding liquid chemical 150 to auxiliary feeder tank 2100, adjusting operation of heater(s) 2110, adjusting air flow velocity controller 108 to adjust static pressure, and the like.

Figure 22:
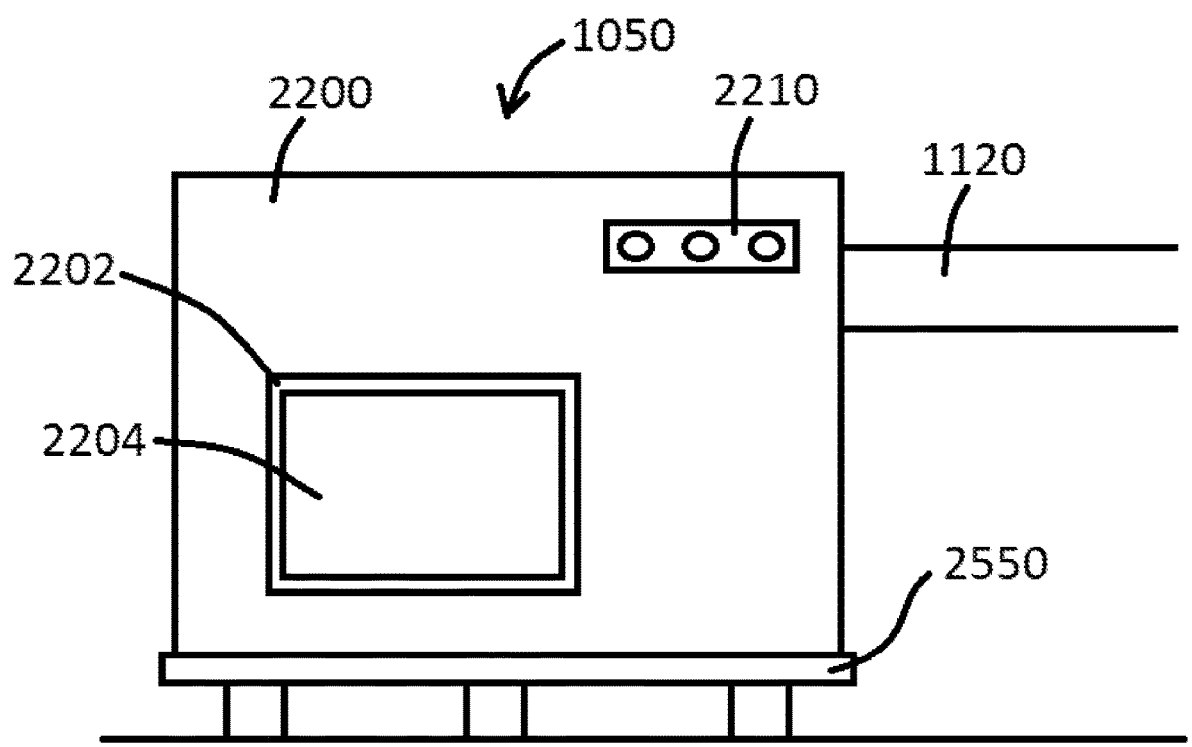

FIG. 22 shows an exemplary system 1050 of the present disclosure, whereby various components of systems 100, 1000 are contained within an outer housing 2200. System 100 components and some system 1000 components can be contained within outer housing 2200, while portions of outlet conduit 1120 extend from outer housing 2200 so to allow volatilized/vaporized liquid chemical 150 to be distributed as desired. Air flow into system occurs via housing vent 2202, and an optional filter 2204 can be used at housing vent 2202 to filter air. An indicator panel 2210 can be present upon outer housing 2200 to indicate various power and/or other levels of systems 100, 1000, 1050 as referenced herein. Housing 2200 helps protect portions of overall system 1050 positioned within housing from the elements, such as heat, rain, snow, ice, etc.

Figure 23:
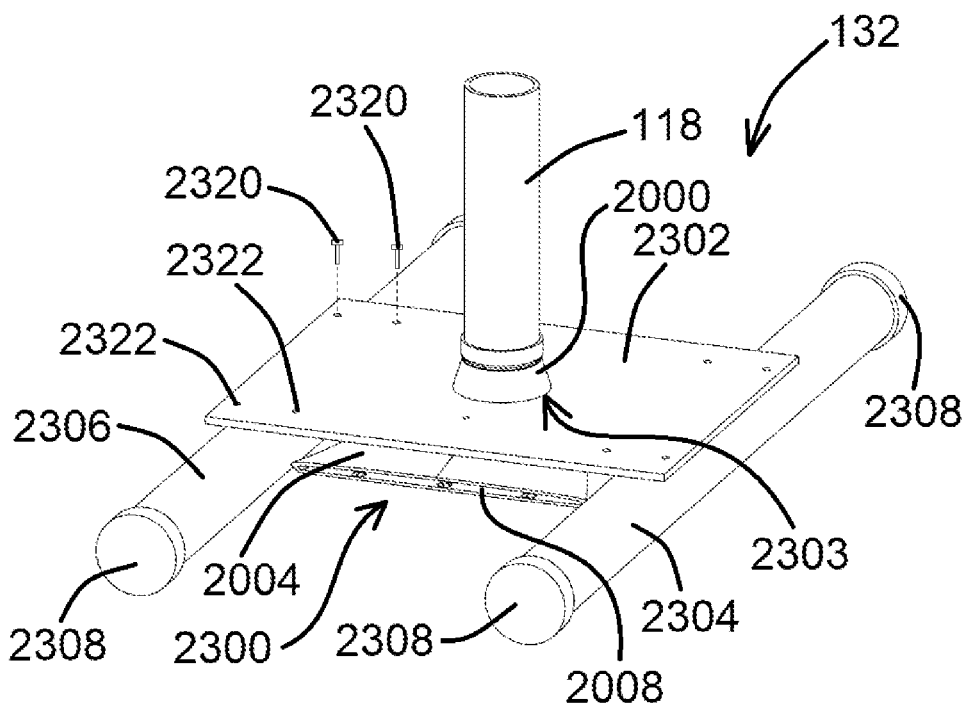
FIG. 23 shows a flotation element with a support panel, according to an exemplary embodiment of the present disclosure.
Figure 24:
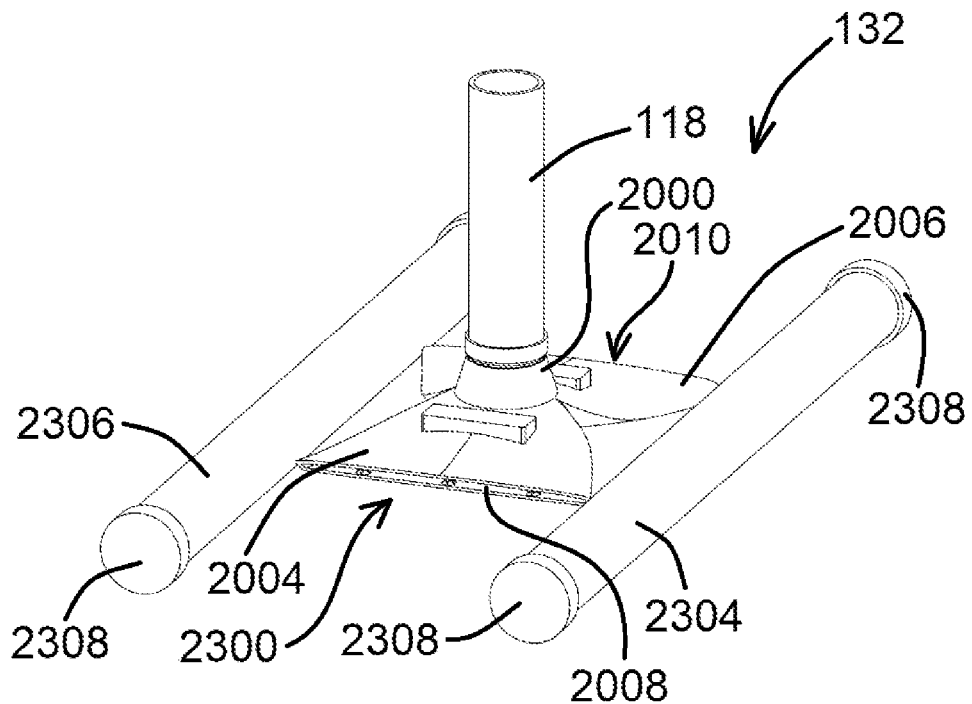
FIG. 24 shows a flotation element with the support panel removed so to be able to see other componentry, according to an exemplary embodiment of the present disclosure.

FIGS. 23 and 24 show various views of exemplary embodiments of flotation elements 132 (also referred to herein as diffusers) of the present disclosure. Referring back to one or more of FIGS. 20A-20D, exemplary flotation elements (which can also be referred to generally as diffusers as noted above) comprise an inlet portion 2000 defining an inlet aperture 2002 therein, first and second outlet portions 2004, 2008, and first and second outlet apertures 2006, 2010 defined therein. The same or similar features can be present in one or more flotation devices 132 shown in FIGS. 23 and 24.

For example, and as shown in FIG. 23, an exemplary flotation device 132 of the present disclosure comprises an inlet portion. 2000 in communication with a diffusion portion 2300, which comprises the first outlet portion 2004 and second outlet portion 2008 noted above. Air, as referenced herein, can pass through inlet aperture 2002, through diffusion portion 2300, and out of first outlet aperture 2306 and second outlet aperture 2300. Support panel 2302, as shown in FIG. 23, is configured to allow fluid communication through inlet portion 2000 and remaining portions of diffusion portion 2300, meaning that some sort of opening (such as aperture 2303) is defined therethrough so to permit said communication. Support panel 2302, such as shown in FIG. 23, is configured to engage one or more buoyant elements 2304, 2306, which can be configured as tubes (as shown, having ends enclosed using end caps 2308), whereby buoyant elements 2304, 2306 are configured to then float on a surface 152 of liquid chemical 150 positioned within tank 102, as referenced herein.

When assembled, an exemplary flotation device 132 of the present disclosure may comprise a diffusion portion 2300, a support panel 2302, and two buoyant elements 2304, 2306 each coupled to opposite relative ends of support panel 2302, such as by way of one or more fasteners 2320 positioned through one or more apertures 2322 defined within support panel 2302 and into buoyant elements 2304, 2306.

FIG. 24 shows the same flotation element 132 shown in FIG. 23, but without support panel 2302. As shown therein, the first outlet portion 2004 and the second outlet portion 2008 can be seen, whereby first outlet aperture 2006 and second outlet aperture 2010 direct the flow of air across a surface 152 of liquid chemical 150 in opposite directions.

Figure 25:
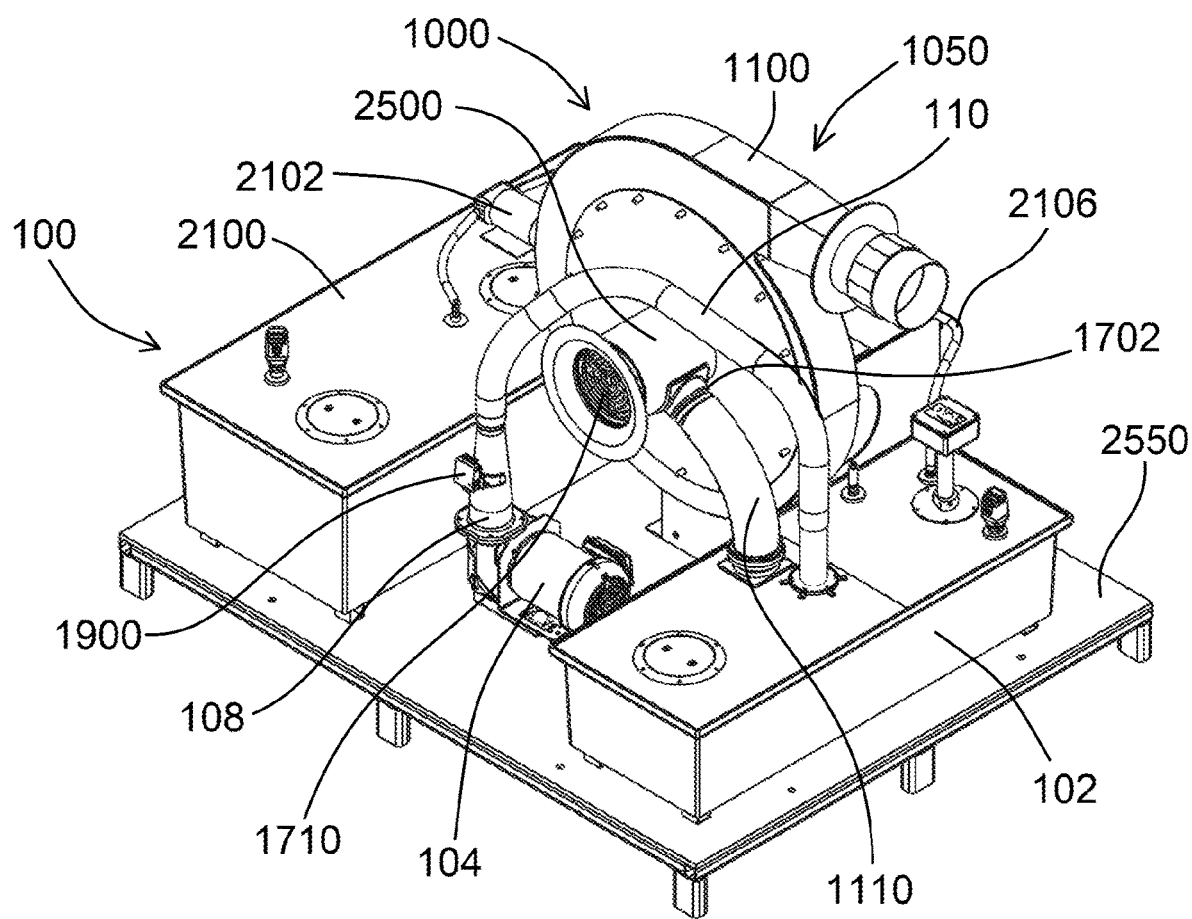
FIG. 25 shows a perspective view of an overall system positioned upon a platform, according to an exemplary embodiment of the present disclosure.

FIG. 25 shows components of an overall system 1050 of the present disclosure comprising a vapor generation system 100 and a vapor distribution system 1000, according to an exemplary embodiment of the present disclosure. As shown therein, chemical 150 can be transferred from auxiliary feeder tank 2100 via operation of pump 2102, through a pump distribution tube 2106, and into tank 102, at approximately the same rate as chemical 150 from within tank 102 is volatilized/vaporized. Volatilized/vaporized chemical 150 can then enter air flow generator 1100 via inlet conduit 1110, and ultimately be distributed by the associated vapor distribution system 1000.

As shown in FIG. 25, inlet conduit 1110 is in vapor communication with tank 102 and intake 2500. Intake 2500, as shown in FIG. 25, can be bell-shaped or have another shape, extending from air flow generator 1100 such that volatilized/vaporized chemical 150 enters intake 2500 instead of entering directly into air flow generator 1100. As air flow generator 1100 operates at relatively low CFM and relatively high pressure, such a configuration (using intake 2500) removes the potential of air flow (volatilized/vaporized chemical 150 flow) in the wrong direction, namely outward instead of inward into air flow generator 1100. Such a configuration does not therefore create any significant vacuum; instead, it operates based on the air pressure coming in, which corresponds to the air pressure generated using air flow generator 104. Chemical 150 from auxiliary feeder tank 104 is naturally aspirated into tank 102, which is volatilized/vaporized, and is able to then enter intake 2500 via inlet conduit 1110. Vapor generation system 100 and vapor distribution system 1000, as shown in FIG. 25, can be positioned upon a platform 2550, such as to facilitate ease of construction, transportation, and/or placement of said systems 100, 1000 to a desired location.

Figure 26:
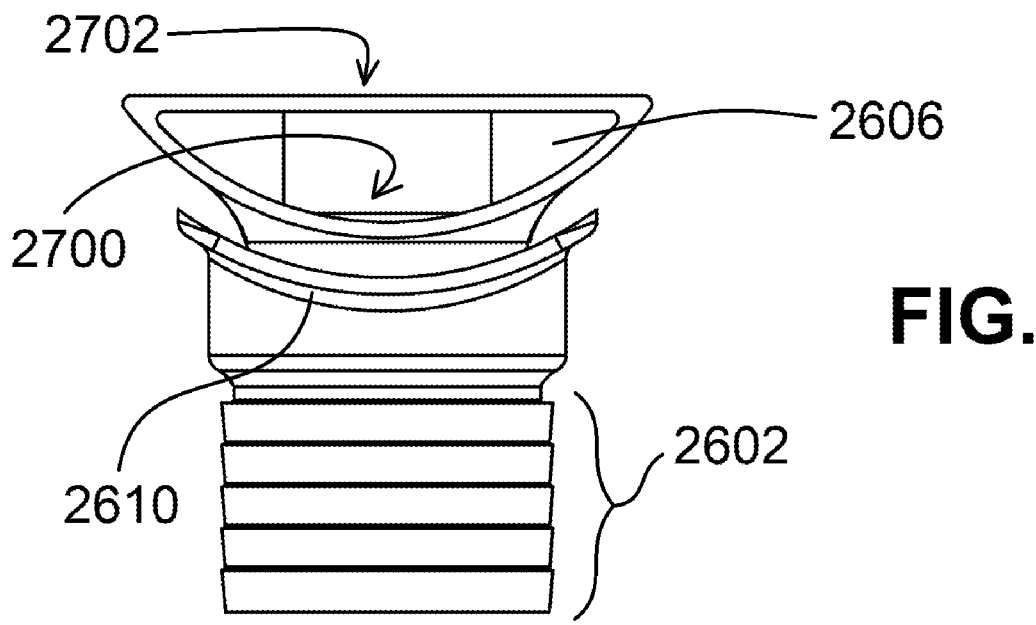
FIG. 26 shows a front view of a nozzle, according to an exemplary embodiment of the present disclosure.
Figure 27:
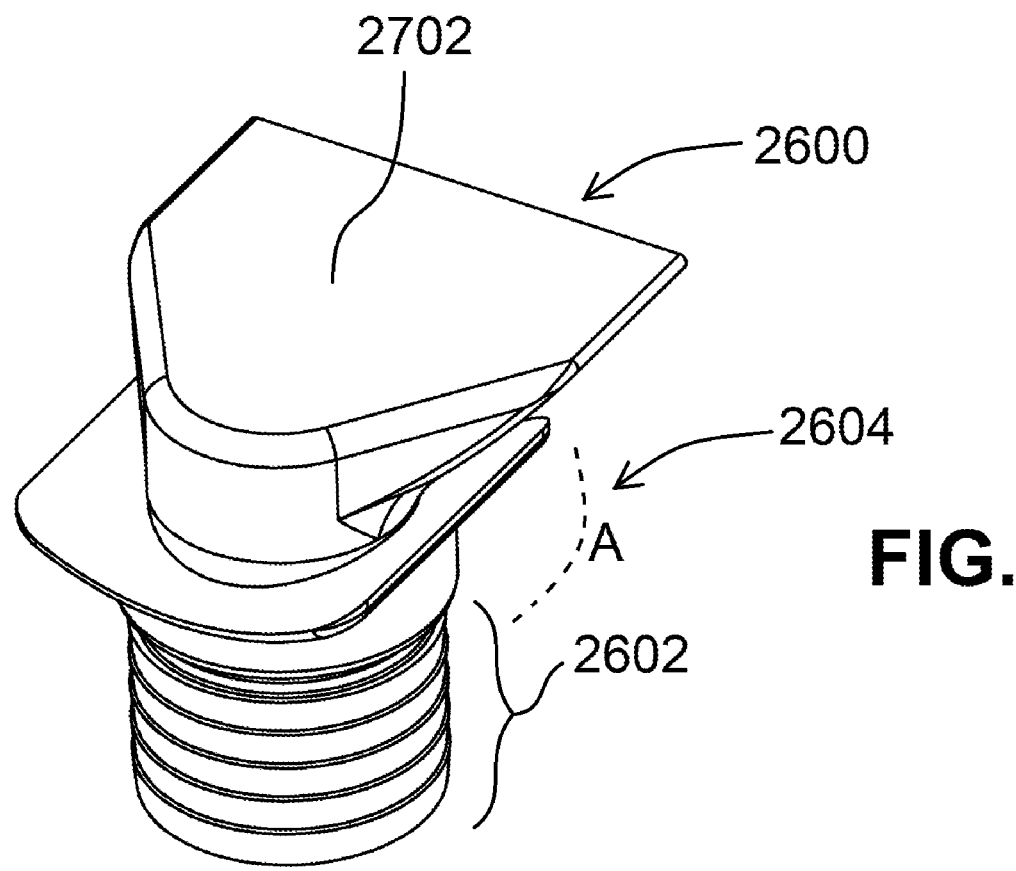
FIG. 27 shows a rear perspective view of a nozzle, according to an exemplary embodiment of the present disclosure.
Figure 28:
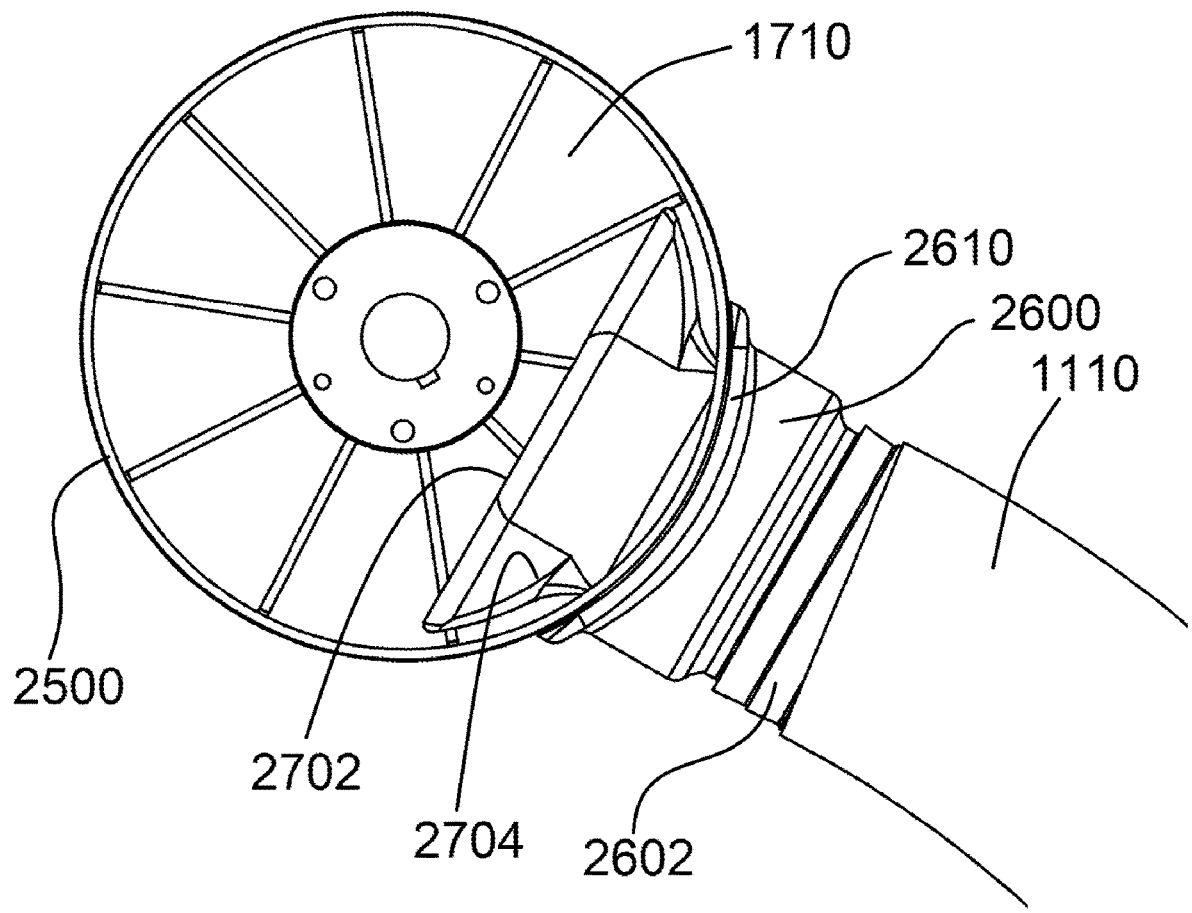
FIG. 28 shows a nozzle connected to an intake of an air flow generator, according to an exemplary embodiment of the present disclosure.

FIG. 26 shows an exemplary embodiment of a nozzle 2600 of the present disclosure. As shown therein, nozzle 2600 is configured for coupling to inlet conduit 1110 at intake 2500, such that when coupled/connected, volatilized/vaporized chemical 150 from tank 102 can enter inlet conduit 1110 and exit inlet conduit 1110 at nozzle 2600 within intake 2500. Nozzles 2600 of the present disclosure have a connection portion 2602 configured to facilitate connection of nozzles 2600 to inlet conduits 1110, such as whereby connection portion 2602 fits within an opening of inlet conduit 1110 and is held in place due to tension, for example. Exemplary nozzles 2600 of the present disclosure can also have one or both of a bend (see bend location 2604 in FIG. 27), such as a 90° bend or a bend of at least 45° up to and including 90° (with bend 2604 identified in FIG. 27 as being angle A), and can have an outlet 2606, such as an outlet 2606 having a half-circle configuration. Outlet 2606 configurations are not limited to any particular design, but it is noted that the half-circle configuration is the preferred configuration as it maximizes the flow of volatilized/vaporized chemical 150 into intake 2500 and into air flow generator 1100 for ultimate distribution, while minimizing the amount of "lost" volatilized/vaporized chemical 150 out of intake 2500 that does not go into air flow generator.

The half-circle configuration of nozzle 2600 at outlet 2606 allows said nozzle 2600 to more closely align with the circular configuration of an exemplary intake 2500 of the present disclosure. For example, and as shown in FIG. 26 and FIG. 28, a first portion 2700 of nozzle 2600 at outlet 2606 is curved so to align with a curvature of an inside of intake 2500, and a second portion 2702 of nozzle 2600 at outlet 2606 is flat so that it can best direct the flow of volatilized/vaporized chemical 150 into air flow generator 1100 while minimizing loss as noted above. Furthermore, an outer curved flange 2610, such as shown in FIGS. 26 and 28, is present and configured so that a first portion 2700 of nozzle 2600 at outlet 2606 is curved so to align with a curvature of an inside of intake 2500, and so that the outer curved flange 2610 is present and configured for positioning outside intake 2500, helping keep nozzle 2600 in place.

Various vapor distribution systems 1000 of the present disclosure can be positioned relative to a source of noxious or otherwise offensive odors, taking into account atmospheric air movement. For example, portions of an exemplary vapor distribution system 1000 of the present disclosure can be located upwind or downwind, as may be desired, relative to the source of said odors. Should portions of system 1000 be positioned upwind from said odor source, chemical vapor can be distributed prior to the location and travel over said location to mix and/or otherwise react with said odors to address the odor problem. Should portions of system 1000 be positioned downwind from said odor source, chemical vapor can be distributed as desired when the odors arrive at system 1000 from the odor-causing location to mix and/or otherwise react with said odors to address the odor problem. Any number of relative positions of systems 100, 1000, 1050 of the present disclosure relative to a source of odor are contemplated within the present disclosure.

The present disclosure also includes disclosure of software used to receive/accept parameters/inputs and generate outputs with respect to said inputs, relating to the generation and/or distribution of chemical vapor. Said software 1416 (as a portion of an exemplary simulation system 1400) is described in further detail in connection with the following.

Various techniques and mechanisms of the present disclosure will sometimes describe a connection between two components. Words such as attached, affixed, coupled, connected, and similar terms with their inflectional morphemes are used interchangeably unless the difference is expressly noted or made otherwise clear from the context. These words and expressions do not necessarily signify direct connections, but include connections through mediate components and devices. Indeed, it should be noted that a connection between two components does not necessarily mean a direct, unimpeded connection, as a variety of other components may reside between the two components of note. For example, a workstation may be in communication with a server, but it will be appreciated that a variety of bridges and controllers may reside between the workstation and the server. Consequently, a connection does not necessarily mean a direct, unimpeded connection unless otherwise noted.

Furthermore, wherever feasible and convenient, like reference numerals are used in the figures and the description to refer to the same or like parts or steps. The drawings are in a simplified form and not to precise scale.

The detailed descriptions which follow are presented in part in terms of algorithms and symbolic representations of operations on data bits within a computer memory representing alphanumeric characters or other information. A computer generally includes a processor for executing instructions and memory for storing instructions and data. When a general purpose computer has a series of machine encoded instructions stored in its memory, the computer operating on such encoded instructions may become a specific type of machine, namely a computer particularly configured to perform the operations embodied by the series of instructions. Some of the instructions may be adapted to produce signals that control operation of other machines and thus may operate through those control signals to transform materials far removed from the computer itself. These descriptions and representations are the means used by those skilled in the art of data processing arts to most effectively convey the substance of their work to others skilled in the art.

An algorithm is here, and generally, conceived to be a self-consistent sequence of steps leading to a desired result. These steps are those requiring physical manipulations of physical quantities. Usually, though not necessarily, these quantities take the form of electrical or magnetic pulses or signals capable of being stored, transferred, transformed, combined, compared, and otherwise manipulated. It proves convenient at times, principally for reasons of common usage, to refer to these signals as bits, values, symbols, characters, display data, terms, numbers, or the like as a reference to the physical items or manifestations in which such signals are embodied or expressed. It should be kept in mind, however, that all of these and similar terms are to be associated with the appropriate physical quantities and are merely used here as convenient labels applied to these quantities.

Some algorithms may use data structures for both inputting information and producing the desired result. Data structures greatly facilitate data management by data processing systems, and are not accessible except through software systems. Data structures are not the information content of a memory, rather they represent specific electronic structural elements which impart or manifest a physical organization on the information stored in memory. More than mere abstraction, the data structures are specific electrical or magnetic structural elements in memory which simultaneously represent complex data accurately, often data modeling physical characteristics of related items, and provide increased efficiency in computer operation.

Further, the manipulations performed are often referred to in terms, such as comparing or adding, commonly associated with mental operations performed by a human operator. No such capability of a human operator is necessary, or desirable in most cases, in any of the operations described herein which form part of the embodiments of the present application; the operations are machine operations. Indeed, a human operator could not perform many of the machine operations described herein due, at least in part, to the vast distribution capabilities of the present disclosure.

Useful machines for performing the operations of one or more embodiments hereof include general purpose digital computers or other similar devices. In all cases the distinction between the method operations in operating a computer and the method of computation itself should be recognized. One or more embodiments of the present application relate to methods and apparatus for operating a computer in processing electrical or other (e.g., mechanical, chemical) physical signals to generate other desired physical manifestations or signals. The computer and systems described herein may operate on software modules, which are collections of signals stored on a media that represents a series of machine instructions that enable the computer processor to perform the machine instructions that implement the algorithmic steps. Such machine instructions may be the actual computer code the processor interprets to implement the instructions, or alternatively may be a higher level coding of the instructions that is interpreted to obtain the actual computer code. The software module may also include a hardware component, wherein some aspects of the algorithm are performed by the circuitry itself rather as a result of an instruction.

Some embodiments of the present disclosure also relate to an apparatus or specific hardware for performing the disclosed operations. This apparatus and/or hardware may be specifically constructed for the required purposes or it may comprise a general purpose computer or related hardware as selectively activated, employed, or reconfigured by a computer program stored in the computer. The algorithms presented herein are not inherently related to any particular computer or other apparatus unless explicitly indicated as requiring particular hardware. In some cases, the computer programs may communicate or relate to other programs or equipment through signals configured to particular protocols which may or may not require specific hardware or programming to interact (e.g., in at least one embodiment, the computer programs use a set of predefined APIs (defined below)). In particular, various general purpose machines may be used with programs written in accordance with the teachings herein, or it may prove more convenient to construct at least one more specialized apparatus to perform the required method steps. The required structure for a variety of these machines will appear from the description below.

Embodiments of the present invention may deal with "object-oriented" software, and particularly with an "object-oriented" operating system. The "object-oriented" software is organized into "objects," each comprising a block of computer instructions describing various procedures ("methods") to be performed in response to "messages" sent to the object or "events" which occur with the object. Such operations include, for example, the manipulation of variables, the activation of an object by an external event, and the transmission of one or more messages to other objects.

Messages are sent and received between objects having certain functions and knowledge to carry out processes. Messages may be generated in response to user instructions, for example, by a user activating an icon with a "mouse" pointer or fingertip, thus generating an event. Also, messages may be generated by an object in response to the receipt of a message. When one of the objects receives a message, the object carries out an operation (a message procedure) corresponding to the message and, if necessary, returns a result of the operation. Each object has a region where internal states (instance variables) of the object itself are stored and where the other objects are not allowed to access. One feature of the object-oriented system is inheritance. For example, an object for drawing a "circle" on a display may inherit functions and knowledge from another object for drawing a "shape" on a display.

A programmer "programs" in an object-oriented programming language by writing individual blocks of code each of which creates an object by defining its methods. A collection of such objects adapted to communicate with one another by means of messages comprises an object-oriented program. Object-oriented computer programming facilitates the modeling of interactive systems in that each component of the system can be modeled with an object, the behavior of each component being simulated by the methods of its corresponding object, and the interactions between components being simulated by messages transmitted between objects.

An operator may stimulate a collection of interrelated objects comprising an object-oriented program by sending a message to one of the objects. The receipt of the message may cause the object to respond by carrying out predetermined functions which may include sending additional messages to one or more other objects. The other objects may in turn carry out additional functions in response to the messages they receive, including sending still more messages. In this manner, sequences of message and response may continue indefinitely or may come to an end when all messages have been responded to and no new messages are being sent. When modeling systems utilizing an object-oriented language, a programmer need only think in terms of how each component of a modeled system responds to a stimulus and not in terms of the sequence of operations to be performed in response to some stimulus. Such sequence of operations naturally flows out of the interactions between the objects in response to the stimulus and need not be preordained by the programmer.

Although object-oriented programming makes simulation of systems of interrelated components more intuitive, the operation of an object-oriented program is often difficult to understand because the sequence of operations carried out by an object-oriented program is usually not immediately apparent from a software listing as in the case for sequentially organized programs. Nor is it easy to determine how an object-oriented program works through observation of the readily apparent manifestations of its operation. Most of the operations carried out by a computer in response to a program are "invisible" to an observer since only a relatively few steps in a program typically produce an observable computer output.

In the following description, several terms which are used frequently have specialized meanings in the present context. The term "API" relates to a set of computer instructions and associated data which can be activated directly or indirectly by the user. The terms "windowing environment," "running in windows," and "API-oriented operating system" are used to denote a computer user interface in which information is manipulated and displayed on a video display such as within bounded regions on a raster scanned video display. The terms "network," "local area network," "LAN," "wide area network," or "WAN" mean two or more computers which are connected in such a manner that messages may be transmitted between the computers. In such computer networks, typically one or more computers operate as a "server," which run one or more applications capable of accepting requests from clients and giving responses accordingly. Servers can run on any computer including dedicated computers, which individually are also often referred to as "the server" and typically comprise—or have access to— large storage devices (such as, for example, hard disk drives) and communication hardware to operate peripheral devices such as printers, webcams, or modems. Servers can also be configured for cloud computing, which is Internet-based computing where groups of remote servers are networked to allow for centralized data storage. Such cloud computing systems enable users to obtain online access to computer services and/or other resources despite such users' potentially diverse geographic locations.

Other computers, termed "workstations" or "clients," provide a user interface so that users of computer networks can access the network resources, such as shared data files, common peripheral devices, and inter-workstation communication. Users activate computer programs or network resources to create "processes" which include both the general operation of the computer program along with specific operating characteristics determined by input variables and its environment. Similar to a process is an agent (sometimes called an intelligent agent), which is a process that gathers information or performs some other service without user intervention and on some regular schedule. Typically, an agent, using parameters typically provided by the user, searches locations either on the host machine or at some other point on a network, gathers the information relevant to the purpose of the agent, and presents it to the user on a periodic basis. A "module" refers to a portion of a computer system and/or software program that carries out one or more specific functions and may be used alone or combined with other modules of the same system or program.

The term "desktop" means a specific user interface which presents a menu or display of APIs with associated settings for the user associated with the desktop. When the desktop accesses a network resource, which typically requires an application program to execute on the remote server, the desktop calls an Application Program Interface, or "API" to allow the user to provide commands to the network resource and observe any output. The term "Browser" refers to a program which is not necessarily apparent to the user, but which is responsible for transmitting messages between the desktop and the network server and for displaying and interacting with the network user. Browsers are designed to utilize a communications protocol for transmission of text and graphic information over a worldwide network of computers, namely the "World Wide Web" or simply the "Web." Examples of Browsers compatible with one or more embodiments described in the present application include, but are not limited to, the Chrome browser program developed by Google Inc. of Mountain View, Calif. (Chrome is a trademark of Google Inc.), the Safari browser program developed by Apple Inc. of Cupertino, Calif. (Safari is a registered trademark of Apple Inc.), Internet Explorer program developed by Microsoft Corporation (Internet Explorer is a trademark of Microsoft Corporation), the Opera browser program created by Opera Software ASA, or the Firefox browser program distributed by the Mozilla Foundation (Firefox is a registered trademark of the Mozilla Foundation). Although the following description details operations in terms of a graphic user interface of a Browser, it will be understood that one or more embodiments disclosed in the present disclosure may be practiced with text based interfaces, voice or visually activated interfaces, or any other interfaces now or hereinafter developed that have many of the functions of a graphic based Browser.

Browsers display information which is formatted in a Standard Generalized Markup Language ("SGML") or a HyperText Markup Language ("HTML"), both being scripting languages which embed non-visual codes in a text document through the use of special ASCII text codes. Files in these formats may be easily transmitted across computer networks, including global information networks like the Internet, and allow the Browsers to display text, images, and play audio and video recordings. The Web utilizes these data file formats to conjunction with its communication protocol to transmit such information between servers and workstations. Browsers may also be programmed to display information provided in an eXtensible Markup Language ("XML") file, with XML files being capable of use with several Document Type Definitions ("DTD") and thus more general in nature than SGML or HTML. The XML file may be analogized to an API, as the data and the stylesheet formatting are separately contained (formatting may be thought of as methods of displaying information, thus an XML file has data and an associated method). Similarly, JavaScript Object Notation (JSON) may be used to convert between data file formats.

The terms "personal digital assistant" or "PDA," as defined above, means any handheld, mobile device that combines computing, telephone, fax, e-mail and/or networking features. The terms "wireless wide area network" or "WWAN" mean a wireless network that serves as the medium for the transmission of data between a handheld device and a computer. The term "synchronization" means the exchanging of information between a first device (e.g., a handheld device) and a second device (e.g., a desktop computer), either via wires or wirelessly. Synchronization ensures that the data on both devices are identical (at least at the time of synchronization).

In wireless wide area networks, communication primarily occurs through the transmission of radio signals over analog, digital cellular or personal communications service ("PCS") networks. Signals may also be transmitted through microwaves and other electromagnetic waves. At the present time, most wireless data communication takes place across cellular systems using second generation technology such as code-division multiple access ("CDMA"), time division multiple access ("TDMA"), the Global System for Mobile Communications ("GSM"), Third Generation (wideband or "3G"), Fourth Generation (broadband or "4G"), personal digital cellular ("PDC"), or through packet-data technology over analog systems such as cellular digital packet data (CDPD") used on the Advance Mobile Phone Service ("AMPS").

The terms "wireless application protocol" or "WAP" mean a universal specification to facilitate the delivery and presentation of web-based data on handheld and mobile devices with small user interfaces. "Mobile Software" refers to the software operating system which allows for application programs to be implemented on a mobile device such as a mobile telephone, PDA, tablet, wearable or smartphone. Examples of Mobile Software are Java and Java ME (Java and JavaME are trademarks of Sun Microsystems, Inc. of Santa Clara, Calif.), BREW (BREW is a registered trademark of Qualcomm Incorporated of San Diego, Calif.), Windows Mobile (Windows is a registered trademark of Microsoft Corporation of Redmond, Wash.), Palm OS (Palm is a registered trademark of Palm, Inc. of Sunnyvale, Calif.), Symbian OS (Symbian is a registered trademark of Symbian Software Limited Corporation of London, United Kingdom), ANDROID OS (ANDROID is a registered trademark of Google, Inc. of Mountain View, Calif.), and iPhone OS (iPhone is a registered trademark of Apple, Inc. of Cupertino, Calif.), and Windows Phone 7, etc. "Mobile Apps" refers to software programs written for execution with Mobile Software.

"PACS" refers to Picture Archiving and Communication System (PACS) involving medical imaging technology for storage of, and convenient access to, images from multiple source machine types. Electronic images and reports are transmitted digitally via PACS; this eliminates the need to manually file, retrieve, or transport film jackets. The universal format for PACS image storage and transfer is DICOM (Digital Imaging and Communications in Medicine). Non-image data, such as scanned documents, may be incorporated using consumer industry standard formats like PDF (Portable Document Format) and the like, once encapsulated in DICOM. A PACS typically utilizes a secured network for the transmission of images, workstations and mobile devices for interpreting and reviewing images, and archives for the storage and retrieval of images and reports. When used in a more generic sense, PACS may refer to any image storage and retrieval system.

Now referring to an exemplary system architecture of the present disclosure, FIG. 14 is a high-level block diagram of a computing environment through which aspects of a presently disclosed simulation system and methods may be implemented. FIG. 14 illustrates a simulation system 1400 of the present disclosure comprises one server 1410 and three clients 1412 (represented as 1412A, 1412B, and 1412C in the figure) connected by network 1414. One or more users (not shown), such as users or administrators, can access the system via the one or more clients 1412. Specifically, in at least one embodiment, the system 1400 of the present disclosure is configured such that one or more users can access the particular functionality of and/or data stored within the server 1410 via a user interface (not shown) and the network 1414. The computing environment may be configured similarly to a multi-user site in that numerous parties may register and/or access the server 1410 via multiple—and commonly remote—clients 1412. The server 1410 is operatively coupled with the clients 1412 over a network 1414 or networking infrastructure. For example and without limitation, the network 1414 may be operatively coupled with clients 1412 via the Internet, intranet or other connection.

It will be appreciated that only three clients 1412A, 1412B, and 1412C are shown in FIG. 14 in order to simplify and clarify the description and the same is not intended to be limiting. Indeed, embodiments of the computing environment may have thousands or millions of clients 1412 connected to network 1414, for example the Internet. Likewise, while only one server 1410 is depicted in FIG. 14, the computing environment may comprise a plurality of servers 1410.

The clients 1412 may each comprise one or more network accessible devices that are capable of executing one or more applications and/or accessing a web-based system through a Browser. A client 1412 may be any type of workstation such as, for example, any type of computer, computing device, or system of a type known in the art such as a personal computer, mainframe computer, workstation, notebook, tablet or laptop computer or device, PDA, mobile telephone or smartphone, wearable, or any other computing or communications device having network interfaces (wireless or otherwise). Additionally, users (not shown) may operate software 1416 (shown as software 1416A, 1416B, and 1416C in the figure) on one or more of clients 1412 to both send and receive messages over the network 1414 via server 1410 and any of its associated communications equipment and software (not shown). Further, clients 1412 may each comprise hardware and componentry as would occur to one of skill in the art such as, for example, one or more microprocessors, memory, input/output devices, device controllers, and the like. Clients 1412 may also comprise one or more input devices that are operable by a user of the client 1412 such as, for example, a keyboard, keypad, pointing device, mouse, touchpad, touch screen, microphone, camera, webcam, and/or any other data entry means (or combination thereof) known in the art or hereinafter developed. Furthermore, client 1412 may also comprise visual and/or audio display means for displaying or emitting output. For example, a client 1412 may comprise a CRT display, an LCD display, a printer, one or more speakers, and/or any other types of display or output devices known in the art or hereinafter developed. The exact configuration of each client 1412 in any particular implementation of a simulation system 1400 hereof may vary between clients 1412 and may be left to the discretion of the practitioner.

As shown in FIG. 14, each client 1412 is connected to, and/or in communication with, the server 1410 via a network 1414. The network 1414 providing access to and/or serving as part of an exemplary simulation system 1400 of the present disclosure comprises any means for interconnecting the server 1410 and a client 1412. In at least one exemplary embodiment, the network 1414 comprises the Internet, a global computer network. Alternatively, the network 1414 may be selected from a variety of different networks and/or cables including, but not limited to, a commercial telephone network, one or more local area networks, one or more wide area networks, one or more wireless communications networks, coaxial cable(s), fiber optic cable(s), and/or twisted-pair cable(s). Additionally, the network 1414 may comprise equivalents of any of the aforementioned, or combinations of two or more types of networks and/or cables.

Furthermore, in at least one embodiment where the server 1410 and a client 1412 comprise a single computing device operable to perform the functions delegated to both server 1410 and a client 1412 according to the present disclosure, the network 1414 may comprise the hardware and software means interconnecting the server 1410 and client 1412 within the single computing device. Accordingly, the network 1414 may comprise packet-switched facilities (such as the Internet), circuit-switched facilities (such as the public-switched telephone network), radio-based facilities (such as a wireless network), or any other facilities capable of interconnecting a client 1412 with the server 1410. Additionally, the clients 1412 and/or wired/wireless connections may include the appropriate safeguards to ensure that the transmission of data between the server 1410 and each client 1412 is secure.

It will be appreciated that where the computing environment comprises a plurality of clients 1412, such clients 1412 need not all comprise the same type of client 1412 or be in communication with the network 1414 and/or server 1410 via the same type of communication link. As such, the computing environment 1400 may comprise some clients 1412 configured to connect to/communicate with the server 1410 via the Internet, for example, while other clients 1412 are connected to the server 1410 via a wired connection (e.g., a cable).

The simulation system 1400 of the present disclosure may be implemented through any appropriate application architecture pattern now known or hereinafter developed. In at least one exemplary embodiment, the simulation system 1400 is delivered through an n-tier architecture in which presentation, application/business logic, and data management functions are logically and/or physically separated. This application architecture pattern provides benefits in the way of increasing availability of the system 1400 to its users (i.e. reduced downtime), the minimization of the impact of any component failure, and through facilitating disaster recovery. Additionally, if desired, third party applications may be interfaced with the system 1400 and provided to system users without sacrificing data security as such third party applications need not be in direct communication with the data structures of the system 1400.

As described above, the clients 1412 of the computing environment each comprise a user interface (not shown) to facilitate a user's input into and access to the functionality of and/or data stored within the server 1410. The user interface can be any interface known in the art that is appropriate to achieve such a purpose and is fully customizable. The user interface may be local to a client 1412, provided over the network 1414, or stored within the server 1410. In at least one embodiment, the user interface comprises a web-based portal that provides functionality for accessing and displaying data stored within the server 1410. In at least one exemplary embodiment, the user interface comprises a mobile application and/or widget designed to run on smartphones, tablet computers, wearables, and other mobile devices.

The simulation system 1400 need not be limited geographically. Users from all over the world can participate, if desired, as there is no inherent restriction as to the number of users who can access and use the simulation system 1400 at a single time. In at least one exemplary embodiment, the simulation system 1400 is delivered as an open platform environment, where anyone with access to the Internet may register as a user of the system 1400. Accordingly, by entering a publicly available website, a user can register and gain access to the functionality provided by the simulation system 1400.

Figure 15:
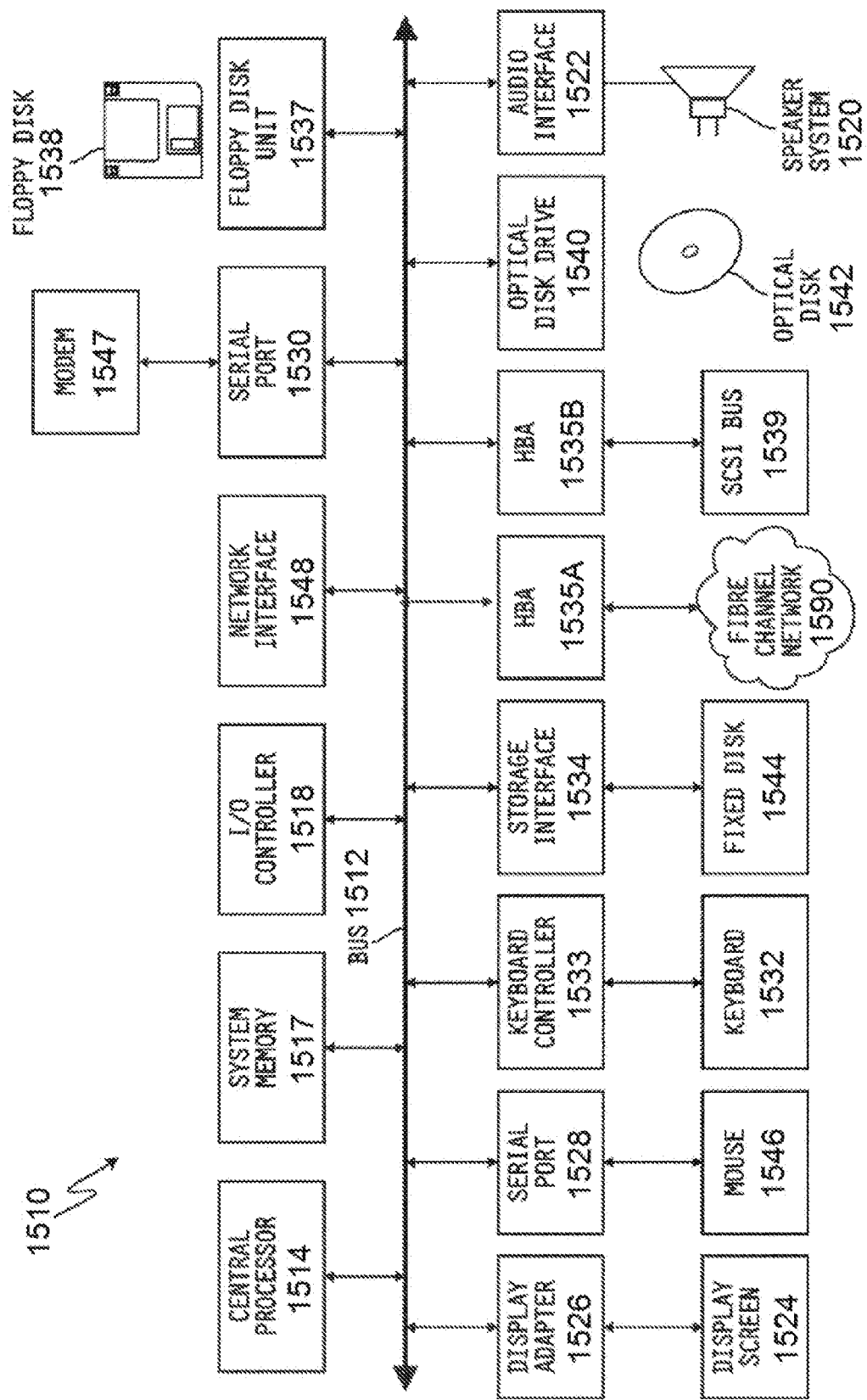
FIG. 15 shows a block diagram of a computing system and various connections therein which may be utilized in connection with embodiments of the present disclosure, according to an exemplary embodiment of the present disclosure.
Figure 16:
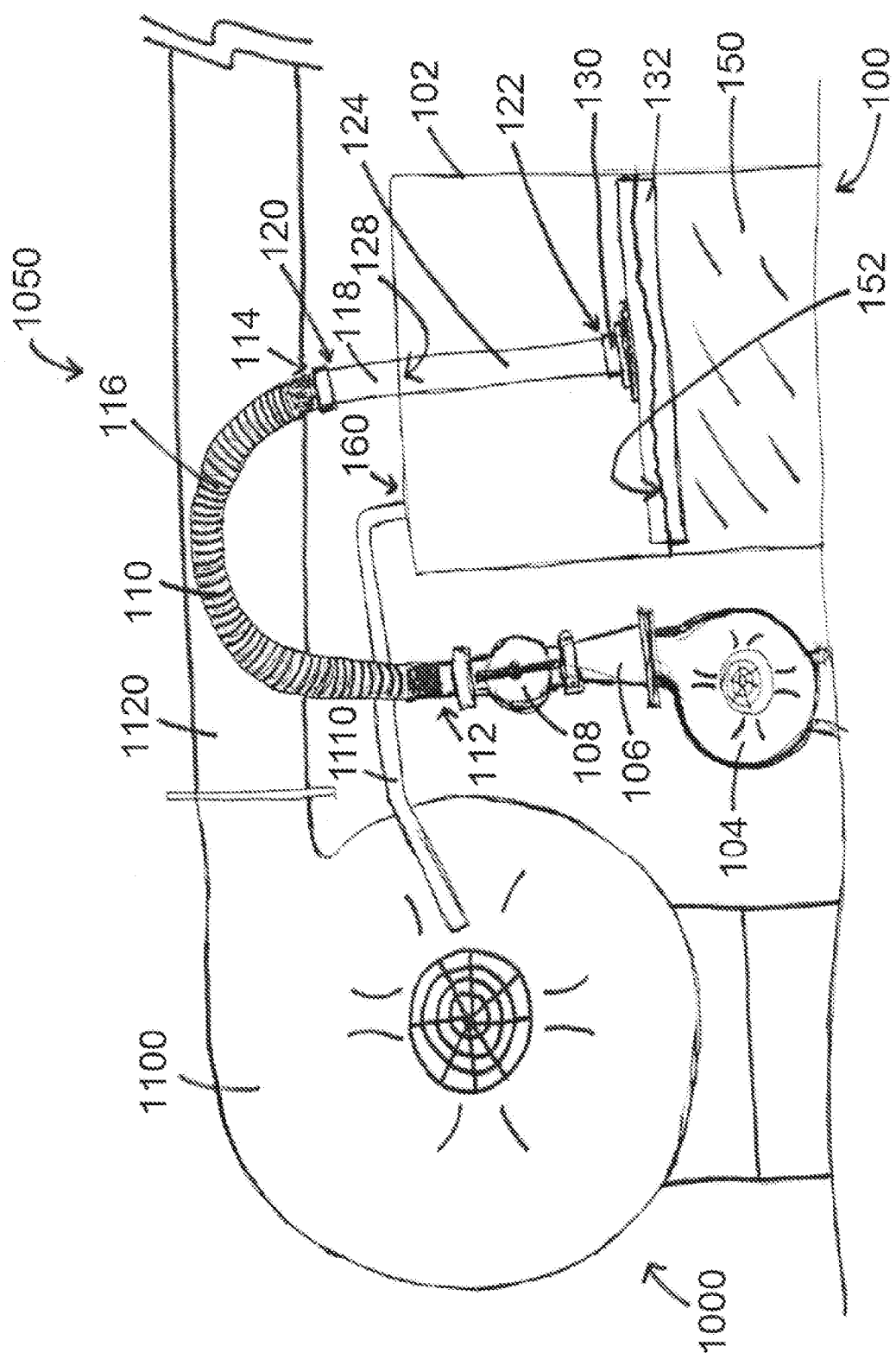
FIGS. 16, 17, 18, and 19 show components of overall systems comprising vapor generation systems and vapor distribution systems, according to exemplary embodiments of the present disclosure.
Figure 17:
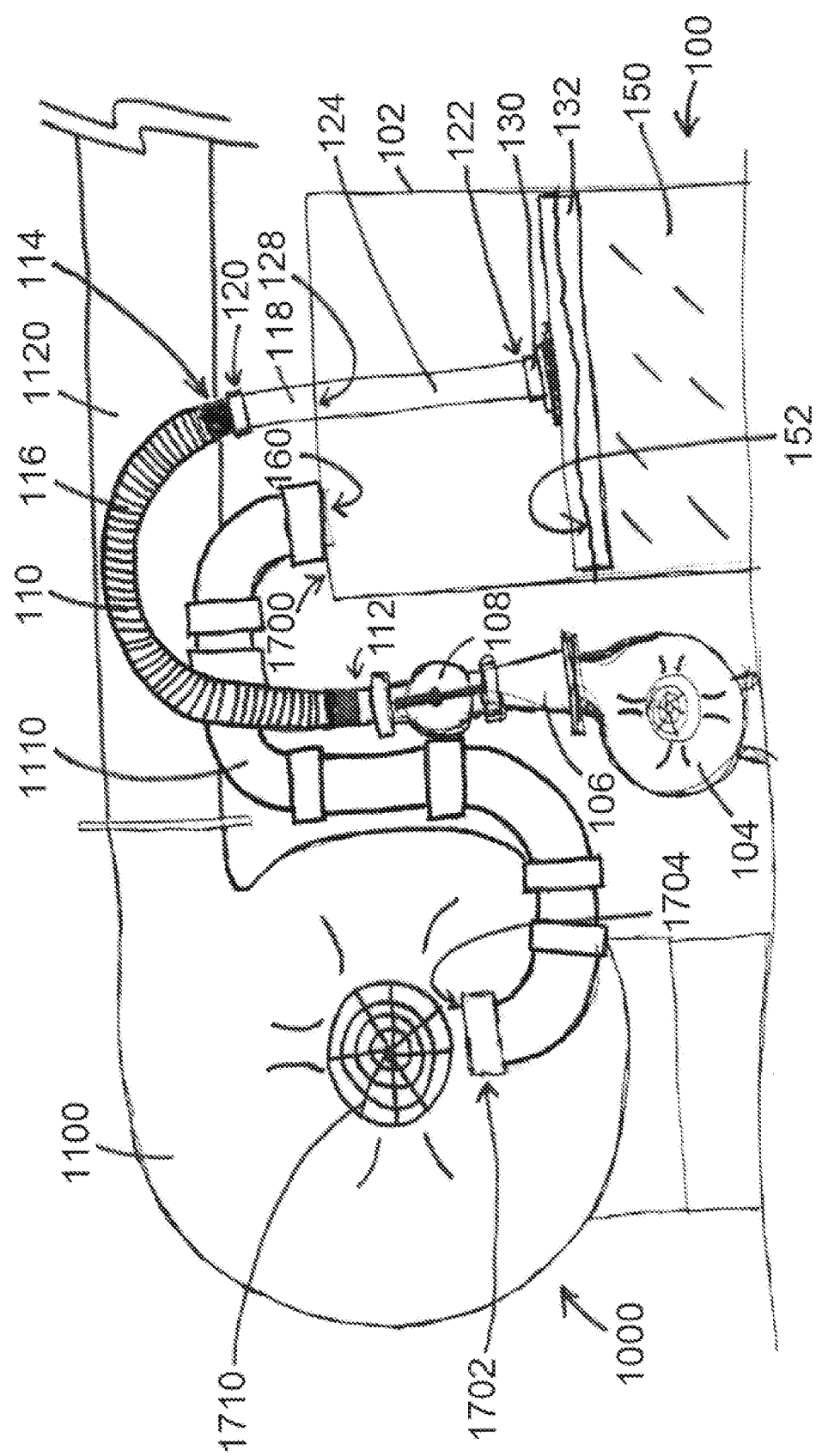

Now referring to FIG. 15, a block diagram of a computer system 1510 suitable for implementing the simulation system 1400 via server 110 or client 1412 is shown. Computer system 1510 includes bus 1512 that interconnects major subsystems of computer system 1510, such as central processor 1514, system memory 1517 (typically RAM, but which may also include ROM, flash RAM, or the like), input/output controller 1518, external audio device, such as speaker system 1520 via audio output interface 1522, external device, such as display screen 1524 via display adapter 1526, serial ports 1528 and 1530, keyboard 1532 (interfaced with keyboard controller 1533), storage interface 1534, disk drive 1537 operative to receive floppy disk 1538, host bus adapter (HBA) interface card 1535A operative to connect with Fibre Channel network 1590, HBA interface card 1535B operative to connect to SCSI bus 1539, and optical disk drive 1540 operative to receive optical disk 1542. Also included are mouse 1546 (or other point-and-click device, coupled to bus 1512 via serial port 1528), modem 1547 (coupled to bus 1512 via serial port 1530), and network interface 1548 (coupled directly to bus 1512).

Bus 1512 allows data communication between central processor 1514 and system memory 1517, which may include read-only memory (ROM) or flash memory (neither shown), and random access memory (RAM) (not shown), as previously noted. RAM is generally the main memory into which operating system and application programs are loaded. ROM or flash memory may contain, among other software code, Basic Input-Output system (BIOS) which controls basic hardware operation such as interaction with peripheral components. Applications resident with computer system 1510 are generally stored on and accessed via computer readable media, such as hard disk drives (e.g., fixed disk 1544), optical drives (e.g., optical drive 1540), floppy disk unit 1537, or other storage medium. Additionally, applications may be in the form of electronic signals modulated in accordance with the application and data communication technology when accessed via network modem 1547 or interface 1548 or other telecommunications equipment (not shown).

Storage interface 1534, as with other storage interfaces of computer system 1510, may connect to standard computer readable media for storage and/or retrieval of information, such as fixed disk drive 1544. Fixed disk drive 1544 may be part of computer system 1510 or may be separate and accessed through other interface systems. Modem 1547 may provide direct connection to remote servers via telephone link or the Internet via an internet service provider (ISP) (not shown). Network interface 1548 may provide direct connection to remote servers via direct network link to the Internet via a POP (point of presence). Network interface 1548 may provide such connection using wireless techniques, including digital cellular telephone connection, Cellular Digital Packet Data (CDPD) connection, digital satellite data connection or the like.

Many other devices or subsystems (not shown) may be connected in a similar manner (e.g., document scanners, digital cameras, and so on). Conversely, all of the devices shown in FIG. 15 need not be present to practice the present disclosure. Furthermore, devices and subsystems may be interconnected in different ways from that shown in FIG. 15. Operation of a computer system such as that shown in FIG. 15 is readily known in the art and is not discussed in detail in this application. Software source and/or API specifications to implement the present disclosure may be stored in computer-readable storage media such as one or more of system memory 1517, fixed disk 1544, optical disk 1542, or floppy disk 1538. The operating system provided on computer system 1510 may be a variety or version of either MS-DOS® (MS-DOS is a registered trademark of Microsoft Corporation of Redmond, Wash.), WINDOWS® (WINDOWS is a registered trademark of Microsoft Corporation of Redmond, Wash.), OS/2® (OS/2 is a registered trademark of International Business Machines Corporation of Armonk, N.Y.), UNIX® (UNIX is a registered trademark of X/Open Company Limited of Reading, United Kingdom), Linux® (Linux is a registered trademark of Linus Torvalds of Portland, Oreg.), or other known or developed operating system. In some embodiments, computer system 1510 may take the form of a tablet computer, typically in the form of a large display screen operated by touching the screen. In tablet computer alternative embodiments, the operating system may be iOS® (iOS is a registered trademark of Cisco Systems, Inc. of San Jose, Calif., used under license by Apple Corporation of Cupertino, Calif.), Android® (Android is a trademark of Google Inc. of Mountain View, Calif.), Blackberry® Tablet OS (Blackberry is a registered trademark of Research In Motion of Waterloo, Ontario, Canada), webOS (webOS is a trademark of Hewlett-Packard Development Company, L.P. of Texas), and/or other suitable tablet operating systems.

Moreover, regarding the signals described herein, those skilled in the art will recognize that a signal may be directly transmitted from a first block to a second block, or a signal may be modified (e.g., amplified, attenuated, delayed, latched, buffered, inverted, filtered, or otherwise modified) between blocks. Although the signals of the certain embodiments described herein are characterized as transmitted from one block to the next, other embodiments of the present disclosure may include modified signals in place of such directly transmitted signals as long as the informational and/or functional aspect of the signal is transmitted between blocks. To some extent, a signal input at a second block may be conceptualized as a second signal derived from a first signal output from a first block due to physical limitations of the circuitry involved (e.g., there will inevitably be some attenuation and delay). Therefore, as used herein, a second signal derived from a first signal includes the first signal or any modifications to the first signal, whether due to circuit limitations or due to passage through other circuit elements which do not change the informational and/or final functional aspect of the first signal.

An exemplary simulation system 1400 can utilize software 1416, as referenced herein, to provide flow simulation modeling as may be desired for a particular vapor generation system 100 and/or vapor distribution system 1000 of the present disclosure. For example, software 1416 can utilize one or more inputs such as ambient air temperature, dew point, location elevation, latitude and longitude, diameter of distribution conduit 1120, length of distribution conduit 1120, number of apertures 1130, size of apertures 1130, flow rate of air flow generator 1100, operating pressure, etc., and generate one or more outputs, such as air density (pounds per cubic foot), air viscosity, Reynolds number, initial air/vapor velocity, kinetic energy, friction factors, flow per aperture 1130 (in CFM), mass flow per aperture 1130 (in pounds per hour), aperture 1130 velocity, etc. For a given length and diameter of distribution conduit 1120 with a specified number and size of apertures 1130, said outputs can be generated using software 1416. In view of the same, the present disclosure includes disclosure of s simulation system 1400, using software 1416, to generate various outputs using various inputs as referenced herein, so that configurations of vapor generation systems 100 and/or vapor distribution systems 1000 of the present disclosure can be determined and ultimately constructed and used as desired.

While various embodiments of vapor generation and distribution devices and systems and methods for using the same to generate and distribute vapor have been described in considerable detail herein, the embodiments are merely offered as non-limiting examples of the disclosure described herein. It will therefore be understood that various changes and modifications may be made, and equivalents may be substituted for elements thereof, without departing from the scope of the present disclosure. The present disclosure is not intended to be exhaustive or limiting with respect to the content thereof.

Further, in describing representative embodiments, the present disclosure may have presented a method and/or a process as a particular sequence of steps. However, to the extent that the method or process does not rely on the particular order of steps set forth therein, the method or process should not be limited to the particular sequence of steps described, as other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. A system, comprising:
   an air flow generator configured to generate a flow of air;
   a first outlet conduit configured to deliver the flow of air from the air flow generator into a tank having a quantity of liquid chemical therein; and
   a flotation element positioned within the tank and defining an aperture therein, the flotation element comprising:
   at least two buoyant elements configured to float upon the quantity of liquid chemical within the tank;
   a support panel having an aperture defined therethrough, the support panel configured for coupling to the at least two buoyant elements and further configured to receive at least part of a diffusion portion therethrough; and
   the diffusion portion comprising an inlet aperture, a first outlet portion, and a second outlet portion opposite the first outlet portion;
   the flotation element configured so that the flow of air from the first outlet conduit passes through the inlet aperture of the diffusion portion and out of the first outlet portion and the second outlet portion to direct the flow of air horizontally across the surface of the liquid chemical;
   wherein the flow of air causes at least a portion of the quantity of liquid chemical to volatilize or vaporize as volatilized or vaporized chemical and exit the tank from a tank aperture.

2. The system of claim 1, wherein the flotation element is configured so that when portions of the flotation element are floating upon the quantity of liquid chemical, a distance between the inlet aperture of the diffusion portion and the surface of the quantity of liquid chemical remains constant or generally constant.

3. The system of claim 1, wherein the inlet aperture of the diffusion portion of the flotation element is located so that when portions of the flotation element are floating upon the quantity of liquid chemical, a distance exists between the inlet aperture and a surface of the quantity of liquid chemical.

4. The system of claim 1, further comprising:
   an air flow velocity controller positioned between the air flow generator and the first outlet conduit, the air flow velocity controller configured to control a rate of the flow of air from the air flow generator prior to the flow of air entering the first outlet conduit.

5. The system of claim 1, further comprising:
   a second outlet conduit coupled to the first outlet conduit and the flotation element, the second outlet conduit configured to fit within and slidingly engage a conduit aperture defined within the tank or defined within a tank lid.

6. The system of claim 1, further comprising:
   an air flow reducer positioned between the air flow generator and the first outlet conduit, the air flow reducer configured to concentrate the flow of air from the air flow generator prior to the flow of air entering the first outlet conduit;
   an air flow velocity controller positioned between the air flow reducer and the first outlet conduit, the air flow velocity controller configured to control a rate of the flow of air from the air flow generator prior to the flow of air entering the first outlet conduit; and
   a second outlet conduit coupled to the first outlet conduit and the flotation element, the second outlet conduit configured to fit within and slidingly engage a conduit aperture defined within the tank or defined within a tank lid;
   wherein the flow of air from the air flow generator, during operation of the air flow generator, passes through the air flow reducer, through the air flow velocity controller, through the first outlet conduit, through the second outlet conduit, and through the inlet aperture of the diffusion portion of the flotation element and onto the surface of the liquid chemical.

7. The system of claim 1, further comprising:

a second air flow generator having an inlet and positioned relative to the tank;

an inlet conduit having a proximal end and a distal end defining a distal opening, the proximal end of the inlet conduit coupled to the tank at a tank aperture and the distal opening positioned relative to the inlet of the second air flow generator;

an intake extending from the inlet of the second air flow generator; and a nozzle positioned at the distal opening of the distal end of the inlet conduit;

the second air flow generator configured to receive the volatilized or vaporized chemical from the tank through the inlet conduit and through the nozzle to an inside of the intake and ultimately into the inlet of the second air flow generator and to distribute the volatilized or vaporized chemical through a distribution conduit coupled to the second air flow generator.

8. The system of claim 7, wherein the second air flow generator comprises a motor positioned within a housing, and wherein the inlet of the second air flow generator is defined within the housing.

9. The system of claim 7, wherein the distribution conduit has a plurality of apertures defined therein.

10. The system of claim 7, wherein the distribution conduit is coupled to a second distribution conduit, and wherein the second distribution conduit has a plurality of apertures defined therein.

11. The system of claim 4, further comprising:
a gauge configured to measure static pressure, the gauge connected to the system proximal to and distal to the air flow velocity controller.

12. The system of claim 7, further comprising:
a feeder tank having a second quantity of liquid chemical therein; and
a pump having a feeder tube, the pump configured to pump at least some of the second quantity of liquid chemical from the feeder tank through the feeder tube, through a pump distribution tube coupled to the pump or the feeder tube, and into the tank.

13. The system of claim 1, further comprising:
a heater positioned relative to the tank and configured to raise a temperature of the quantity of liquid chemical within the tank.

14. The system of claim 12, further comprising:
a heater positioned relative to the feeder tank and configured to raise a temperature of the second quantity of liquid chemical within the feeder tank.

15. The system of claim 11, wherein the gauge comprises a wireless transmitter configured to transmit pressure data from the gauge to a remote location.

16. The system of claim 12, further comprising:
a level sensor configured to obtain data relating to a level of the quantity of the first chemical within the tank, wherein said data is used to control operation of the pump.

17. The system of claim 12, further comprising:
an air flow reducer positioned between the air flow generator and the first outlet conduit, the air flow reducer configured to concentrate the flow of air from the air flow generator prior to the flow of air entering the first outlet conduit;
an air flow velocity controller positioned between the air flow reducer and the first outlet conduit, the air flow velocity controller configured to control a rate of the flow of air from the air flow generator prior to the flow of air entering the first outlet conduit; and
a second outlet conduit coupled to the first outlet conduit and the flotation element, the second outlet conduit configured to fit within and slidingly engage a conduit aperture defined within the tank or defined within a tank lid;
wherein the flow of air from the air flow generator, during operation of the air flow generator, passes through the air flow reducer, through the air flow velocity controller, through the first outlet conduit, through the second outlet conduit, and through the aperture of the flotation element onto the surface of the liquid chemical; and
wherein the distribution conduit is coupled to a second distribution conduit, and wherein the second distribution conduit has a plurality of apertures defined therein.

18. The system of claim 7, wherein when the distribution conduit or a second distribution conduit coupled thereto is positioned relative to a source of an odor, the volatilized or vaporized chemical distributed by the second air flow generator can exit a plurality of apertures defined within the distribution conduit and/or the second distribution conduit to alleviate the odor.

19. A system, comprising:

a vapor generation system, comprising:

an air flow generator configured to generate a flow of air;

a first outlet conduit configured to deliver the flow of air from the air flow generator into a tank having a quantity of liquid chemical therein; and a flotation element positioned within the tank and defining an aperture therein, the flotation element comprising:

at least two buoyant elements configured to float upon the quantity of liquid chemical within the tank;

a support panel having an aperture defined therethrough, the support panel configured for coupling to the at least two buoyant elements and further configured to receive at least part of a diffusion portion therethrough; and the diffusion portion comprising an inlet aperture, a first outlet portion, and a second outlet portion opposite the first outlet portion;

the flotation element configured so that the flow of air from the first outlet conduit passes through the inlet aperture of the diffusion portion and out of the first outlet portion and the second outlet portion to direct the flow of air horizontally across the surface of the liquid chemical;

wherein the flow of air causes at least a portion of the quantity of liquid chemical to volatilize or vaporize as volatilized or vaporized chemical and exit the tank from a tank aperture; and a vapor distribution system, comprising:

a second air flow generator having an inlet and positioned relative to the tank;

an inlet conduit having a proximal end and a distal end defining a distal opening, the proximal end of the inlet conduit coupled to the tank at a tank aperture and the distal opening positioned relative to the inlet of the second air flow generator;

an intake extending from the inlet of the second air flow generator; and a nozzle positioned at the distal opening of the distal end of the inlet conduit;

the second air flow generator configured to receive the volatilized or vaporized chemical from the tank through the inlet conduit and through the nozzle to an inside of the intake and ultimately into the inlet of the second air flow generator and to distribute the volatilized or vaporized chemical through a distribution conduit coupled to the second air flow generator.

20. A method to generate vapor, comprising the step of:

operating a vapor generation system to generate volatilized or vaporized chemical, the vapor generation system comprising:

an air flow generator configured to generate a flow of air;
a first outlet conduit configured to deliver the flow of air from the air flow generator into a tank having a quantity of liquid chemical therein; and
a flotation element positioned within the tank and defining an aperture therein, the flotation element comprising:
at least two buoyant elements configured to float upon the quantity of liquid chemical within the tank;
a support panel having an aperture defined therethrough, the support panel configured for coupling to the at least two buoyant elements and further configured to receive at least part of a diffusion portion therethrough; and
the diffusion portion comprising an inlet aperture, a first outlet portion, and a second outlet portion opposite the first outlet portion;
the flotation element configured so that the flow of air from the first outlet conduit passes through the inlet aperture of the diffusion portion and out of the first outlet portion and the second outlet portion to direct the flow of air horizontally across the surface of the liquid chemical;
wherein the flow of air causes at least a portion of the quantity of liquid chemical to volatilize or vaporize as volatilized or vaporized chemical and exit the tank from a tank aperture.

* * * * *